US007060486B2

(12) United States Patent
Wood et al.

(10) Patent No.: US 7,060,486 B2
(45) Date of Patent: Jun. 13, 2006

(54) INHIBITION OF SULFATE-REDUCING-BACTERIA-MEDIATED DEGRADATION USING BACTERIA WHICH SECRETE ANTIMICROBIALS

(75) Inventors: Thomas K. Wood, Tolland, CT (US); Arul Jayaraman, Norwood, MA (US); James C. Earthman, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/653,340

(22) Filed: Sep. 2, 2003

(65) Prior Publication Data

US 2005/0250179 A1    Nov. 10, 2005

Related U.S. Application Data

(60) Division of application No. 09/282,277, filed on Mar. 31, 1999, now Pat. No. 6,630,197, which is a continuation-in-part of application No. 09/074,037, filed on May 6, 1998, now abandoned.

(51) Int. Cl.
*C12M 1/00* (2006.01)
*C12M 3/00* (2006.01)

(52) U.S. Cl. ............................... 435/283.1; 435/289.1

(58) Field of Classification Search ............. 435/283.1, 435/289.1

See application file for complete search history.

(56) References Cited

U.S. PATENT DOCUMENTS 5,405,531 A    4/1995    Hitzman et al.

FOREIGN PATENT DOCUMENTS

DE    4127744 A1    2/1993

OTHER PUBLICATIONS

Benbouzid-Rollet et al., "Monitoring of a Vibrio natriegens and Desulfovibio vulgaris marine aerobic biofilm on a stainless steel surface in a laboratory tubular flow system.", *Jour. Applied Bacteriology* 7:244-251 (1991).
Hamilton, "Sulphate-Reducing Bacteria and Anaerobic Corrosion.", *Ann. Rev. Microbiol.* 39:195-217 (1985).
Krause et al., "Molecular Cloning of an Ornithine-Activating Fragment of the Gramicidin S Synthetase 2 Gene from *Bacillus brevis* and its Expression in *Escherichia coli*.", *Jour. Bacteriology* 162:3:1120-1125 (1985).
Abdel-Fatah et al., "Purification and Properties of Penicillinase Enzymes from *Bacillus cereus* and *Pseudomonas fluorescens*.", *Egypt. J. Pharm. Sc.* 35:1-6:519-537 (1994).
Jayaraman et al., "Importance of biofilm formation for corrosion inhibition of SAE 1018 steel by axenic aerobic biofilms.", *Jour. Industrial Microbiology & Biotechnology* 18:396-401 (1997).
Pederson et al., "The Effects of Metal Corrosion by *Serratia marcescens* and a *Pseudomonas SP.*" *Biofouling* 1:313-322 (1989).
Pederson et al., "Inhibition of Metal Corrosion by Bacteria.", *Biofouling* 3:1-11 (1991).
Hernandez et al., "Corrosion Inhibition of Steel by Bacteria.", *Corrosion Science* 50:8:603-608 (1994).
Jack et al., "Differential Corrosion Rates of Carbon Steel by Combinations of *Bacillus* sp., *Hafnia Alvei* and *Desulfovibrio Gigas* Established by Phospholipid Analysis of Electrode Biofilm.", *Corrosion Science*. 33:1943-1853 (1992).

*Primary Examiner*—Mark Navarro
(74) *Attorney, Agent, or Firm*—Townsend and Townsend and Crew LLP

(57) ABSTRACT

The present invention relates to the field of degradation or corrosion prevention or inhibition through the use of bacteria which secrete antimicrobial chemical compositions. In particular, the invention relates to the use of bacteria which, either naturally or through the use of recombinant technology, secrete chemical compositions which inhibit the growth of sulfate-reducing bacteria on metals, concrete, mortar, and other surfaces subject to corrosion.

46 Claims, 9 Drawing Sheets

SEQUENCE LISTING

```
<160> NUMBER OF SEQ ID NOS: 9

<210> SEQ ID NO 1
<211> LENGTH: 69
<212> TYPE: DNA
<213> ORGANISM: Artificial Sequence
<220> FEATURE:
<223> OTHER INFORMATION: Description of Artificial Sequence:
      oligonucleotide used for cloning indolicidin

<400> SEQUENCE: 1
atagaggcta gcgcgatcct tccttggaaa tggccttggt ggccttggcg ccgctaaaag     60
cttatcgac                                                             69

<210> SEQ ID NO 2
<211> LENGTH: 66
<212> TYPE: DNA
<213> ORGANISM: Artificial Sequence
<220> FEATURE:
<223> OTHER INFORMATION: Description of Artificial Sequence:
      oligonucleotide used for cloning bactenecin

<400> SEQUENCE: 2
atagaggcta gcgcgcgtct ttgtcgtatc gttgttatcc gtgtttgtcg ttaaaagctt     60
atcgac                                                                66

<210> SEQ ID NO 3
<211> LENGTH: 25
<212> TYPE: PRT
<213> ORGANISM: Artificial Sequence
<220> FEATURE:
<223> OTHER INFORMATION: Description of Artificial Sequence:pro-
      bactenecin pro-region and bactenecin

<400> SEQUENCE: 3

Ala Lys Thr Glu Thr Ser Ser His Lys Ala His Thr Glu Arg Leu Cys
```

```
            1               5              10              15
Arg Ile Val Val Ile Arg Val Cys Arg
            20              25
```

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:relevant
      nucleotides for cloning pro-bactenecin

<400> SEQUENCE: 4
atagaggcta gcgcggccaa a                                             21

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence:relevant
      nucleotides for cloning pro-bactenecin

<400> SEQUENCE: 5
aaggcacaca cagaaacgtc tttgt                                         25

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence:relevant
      nucleotides for cloning pro-bactenecin

<400> SEQUENCE: 6
gtgtgtgtct ttgcagaaac agca                                          24

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence:relevant
      nucleotides for cloning pro-bactenecin

<400> SEQUENCE: 7
gccggcgttc gaatagctc                                                19

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence:non-amidated
      indolicidin

<400> SEQUENCE: 8

```
Ile Leu Pro Trp Lys Trp Pro Trp Trp Pro Trp Arg Arg
 1               5                  10
```

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence:non-amidated
      bactenecin

```
<400> SEQUENCE: 9

Arg Leu Cys Arg Ile Val Val Ile Arg Val Cys Arg
1               5                   10
```

INHIBITION OF SULFATE-REDUCING-BACTERIA-MEDIATED DEGRADATION USING BACTERIA WHICH SECRETE ANTIMICROBIALS

CROSS-REFERENCES TO RELATED APPLICATIONS

This application is a divisional application of U.S. application Ser. No. 09/282,277, filed Mar. 31, 1999, now U.S. Pat. No. 6,630,197, which was a continuation-in-part of U.S. Ser. No. 09/074,037, filed May 6, 1998, now abandoned. The contents of all of these applications are hereby incorporated by reference.

NON-FEDERAL RESEARCH SUPPORT

The invention described herein was made in the course of or under a contract, RP8044-02, with the Electric Power Research Institute.

STATEMENT AS TO RIGHTS TO INVENTIONS MADE UNDER FEDERALLY SPONSORED RESEARCH AND DEVELOPMENT

Not applicable.

FIELD OF THE INVENTION

The present invention relates to the field of prevention or inhibition of degradation of surfaces susceptible to degradation through the use of bacteria which secrete antimicrobial chemical compositions. In particular, the invention relates to the use of bacteria which, either naturally or through the use of recombinant technology, secrete chemical compositions which inhibit the growth of sulfate-reducing bacteria on metals, concrete, mortar, and other surfaces subject to corrosion or degradation.

BACKGROUND OF THE INVENTION

Degradation and corrosion damage imposes an enormous cost throughout the world. In the United States alone, the annual cost of corrosion damage has been estimated to be equivalent to 4.2% of the gross national product (Martinez, L. *J. Metals.* 45:21 (1993)) (hereafter, Martinez, 1993). These large costs could be greatly reduced by better and wider use of corrosion protection techniques.

Microbes contribute significantly to degradation and corrosion damage. When surfaces, and particularly metals, are exposed to natural environments, they are rapidly colonized by aerobic bacteria present in the bulk liquid phase (Geesey, G. G., What is biocorrosion? Presented at the International workshop on industrial biofouling and biocorrosion, Stuttgart, Germany. Springer-Verlag, New York (1990)) (hereafter, Geesey, 1990). The upper layers of this biofilm are aerobic while the regions near the metal surface are anoxic due to the depletion of oxygen by the biofilm (Blenkinsopp, S. A. et al., *Trends. Biotechnol.* 9:138–143 (1991); Bryers, J. D. et al., *Biotech. Prog.* 3:57–67 (1987)). Sulfate-reducing bacteria ("SRB") can colonize these anaerobic niches and thus contribute to corrosion even in an aerobic environment (Hamilton, W. A. Sulphate-reducing bacteria and their role in biocorrosion. Presented at the International workshop on industrial biofouling and biocorrosion, Stuttgart, Germany. Springer-Verlag (1990)) (hereafter, Hamilton, 1990).

SRB have been implicated in the deterioration of metals in a wide range of environments (Borenstein, S. W. *Microbiologically influenced corrosion handbook.* Woodhead Publishing Limited, Cambridge, England (1994) (hereafter, "Borenstein, 1994"); Hamilton, W. A. *Ann. Rev. Microbiol.* 39:195–217 (1985) (hereafter "Hamilton, 1985"); Hamilton, W. A. *Trends. Biotechnol.* 1:36–40 (1983); Hamilton, 1990). Pipelines and off-shore oil rigs in the oil and shipping industries (Hamilton, W. A. *Trends. Biotechnol.* 1:36–40 (1983)), cooling water recirculation systems in industrial systems (Borenstein, 1994; Miller, J. D. Metals, p. 150–201. In Rose, A. H. (ed.), *Microbial Deterioration*, Academic Press, New York (1981)) (hereafter, Miller, 1981), sewage treatment facilities and pipelines (Hamilton, 1985); Odom, J. M. *ASM NEWS.* 56:473–476 (1990)), jet fuel tanks in the aviation industry (Miller, 1981), and the power generation industry (Licina, G. J. *Mater. Perform.* 28:55–60 (1989)) (hereafter, Licina, 1989) have all been adversely affected by the growth and colonization of SRB. SRB can cause corrosion of a wide range of metals like low-grade carbon steels (e.g., Borshchevskii, A. M. et al., *Prot. Metals.* 30:313–316 (1994); Cheung, C. W. S. and Beech, I. B., *Biofouling.* 9:231–249 (1996) (hereafter, Cheung and Beech, 1996); Dubey, R. S. et al., *Ind. J. Chem. Tech.* 2:327–329 (1995); Gaylarde, C. C. *Int. Biodet. Biodeg.* 30:331–338 (1992)) (hereafter, Gaylarde, 1992); Lee et al., *Biofouling* 7:197–216 (1993); stainless steels, (Benbouzid-Rollet, N. et al., *J. Appl. Bacteriol.* 71:244–251 (1991); Mollica, A. *Int. Biodet. Biodeg.* 29:213–229 (1992); Newman, R. C. et al., *ISIJ International.* 3:201–209 (1991)); Oritz et al., *Int. Biodet.* 26:315–326 (1990)); and copper alloys (Licina, 1989; Wagner, P. and Little, B., *Mater. Perform.* 32:65–68 (1993)) (hereafter, Wagner and Little, 1993), all of which are frequently used in process, shipping, and power industries. SRB also contribute substantially to the degradation of nonmetallic portions of the world's infrastructure. SRB produce hydrogen sulfide, which is then metabolized by sulfur-oxidizing organisms such as *Thiobacillus* into sulfuric acid. Sulfuric acid degradation due to bacteria has been found to reduce dramatically, for example, the service life of concrete conduits in water systems. Corrosion damage due to SRB just of metals in the U.S. has been estimated to amount to some $4–6 billion annually (Beloglazov, S. M. et al., *Prot. Met. USSR.* 27:810–813 (1991)) (hereafter, Beloglazov, 1991).

Conventional corrosion inhibition strategies have included a modification in the pH, redox potential, and resistivity of the soil in which the equipment is to be installed (Iverson, W. P. *Adv. Appl. Microbiol.* 32:1–36 (1987)) (hereafter, Iverson, 1987), inorganic coatings, cathodic protection, and biocides (Jack, T. R. et al., Control in Industrial Settings, p. 265–292. In Barton, L. L. (ed.), *Sulfate-reducing Bacteria.* Plenum Press, New York (1995)) (hereafter, Jack et al., 1995) (the entirety of the Barton reference is hereby incorporated by reference). Inorganic protective coatings like paints and epoxies have been used extensively in the past; but, they are not permanent, and the cost of maintaining and replacing them is substantial (Jayaraman, A., et al., *Appl. Microbiol. Biotechnol.* 47:62–68 (1997) (hereafter, Jayaraman et al., 1997a); Martinez, 1993). With cathodic protection, the cathodic reaction is stimulated on the metal surface by coupling it to a sacrificial anode made of magnesium or zinc, or by supplying an impressed current from an external power supply through a corrosion-resistant anode. The galvanic or impressed current lowers the electrochemical potential everywhere on the metal surface so that metal cations do not form, and no dissolution occurs. ((Iverson, 1987); Little, B. J. et al., *Mater. Perform.* 32:16–20 (1993)). However, Wagner and Little (1993) report that the use of cathodic potentials up to −1074 mV were not able to prevent biofilm formation.

Biocides have also been used to retard the corrosion reaction in closed systems such as cooling towers and storage tanks (Iverson, 1987)) and are probably the most common method of combating biocorrosion (Boivin, J., *Mater. Perform.* 34:65–68 1995) (hereafter, Boivin, 1995); Brunt, K. D., Biocides for the oil industry, p. 201–207, In Hill, E. C., Shennan, J. L., Watkinson, R. J. (ed.), Microbial Problems in the Offshore Oil Industry, John Wiley and Sons, Chichester, England (1986); Cheung, C. W. S. et al., *Biofouling* 9:231–249 (1996)) (hereafter, Cheung, 1996). Saleh et al. (*J. Appl. Bacteriol.* 27:281–293 (1964)) (hereafter, Saleh et al., 1964) reviewed the use of nearly 200 compounds that are bactericidal or bacteriostatic against SRB. Oxidizing biocides like chlorine, chloramines, and chlorinating compounds are used in freshwater systems (Boivin, 1995, supra). Chlorine compounds are the most practical biocides; however, their activity depends on the pH of the water and the extent of light and temperature (Keevil, C. W. et al., *Int. Biodet.* 26:169–179 (1990)) (hereafter, Keevil et al., 1990), and they are not very effective against biofilm bacteria (Boivin, 1995, supra). Non-oxidizing biocides such as quartenary salts (Beloglazov, 1991), amine-type compounds, anthraquinones (Cooling III, F. B. et al., *Appl. Environ. Microbiol.* 62:2999–3004 (1996)) (hereafter, Cooling et al., 1996), and aldehydes (Boivin, 1995) are more stable and can be used in a variety of environments. Use of these biocides suffer from a number of serious drawbacks, including not only cost of the biocides themselves but also the environmental cost of releasing into the water supply large quantities of inorganic compounds.

A further problem is imposed by the organization of the biofilm on the material surface. The glycocalyx (Brown, M. L. et al., *Appl. Environ. Microbiol.* 61:187–193 (1995); Hoyle, B. D. et al., *J Antimicrob. Chemother.* 26:1–6 (1990); Suci, P. A. et al., *Antimicrob. Agents Chemother.* 38:2125–2133 (1994)), phenotypical changes which occur in the biofilm, such as the expression of the algC gene in *P. aeruginosa* (Costerton, W. J. et al., *Ann. Rev. Microbiol.* 49:711–745 (1995)) (hereafter, Costerton, 1995), and the effect of surface chemistry on the metabolic state of the biofilm (Keevil et al., 1990) may all serve to increase the resistance of organisms in a biofilm to antimicrobial agents beyond that observed with planktonic bacteria (Brown, M. R. W. et al., *J. Appl. Bacteriol. Symp. Suppl.* 74:87S-97S (1993)). A combination of an organic film-corrosion inhibitor, a polyacrylate/phosphonate, and two biocides has been used successfully to control corrosion in a cooling water system (Iverson, supra). However, SRB are inherently resistant to a wide range of antimicrobials (Saleh et al., 1964, supra), and the harsh anaerobic environment (created by the corrosion products) in which the SRB thrive also reduces the efficiency of the antimicrobials (Cheung, 1996; Iverson, supra). Once SRB are firmly established in their niche, it is difficult to eliminate them from a system without disassembling it (Boivin, 1995, supra).

Another strategy to control microbially induced corrosion is to suppress the growth of the most harmful microorganisms by manipulating the nutrient availability and thereby create a more benign biofilm (Jack et al., 1995). Recently, Jansen and Kohnen (*J. Ind. Microb.*, 15:391–396 (1995)) reported the reduction in the adherence of *Staphylococcus epidermis* KH6 to surfaces by modifying the polymer surface by ionic bonding of silver ions to the surface and suggested the development of antimicrobial polymers to prevent bacterial adherence. Wood, P., et al. (1996) (*Appl. Environ. Microbiol.* 62:2598–2602) reported the generation of potassium monopersulfate and hydrogen peroxide at the surface by catalysis increased the activity of these biocides 150-fold towards a *P. aeruginosa* biofilm. This method relied on permeating a plastic with the necessary chemical agents, and would require widespread, substantial, and costly changes in manufacturing techniques to implement.

Finally, work by others suggested (Pedersen and Hermansson, *Biofouling*, 1:313–322 (1989), and *Biofouling* 3: 1–11 (1991)), and our own work has recently confirmed (Jayaraman et al., 1997a and Jayaraman et al., *J. Ind. Microb.* 18:396–401 (1997) (hereafter, Jayaraman et al. 1997b), that aerobic bacteria in a biofilm can inhibit electrochemical corrosion of metal by two to forty fold, possibly due in part to the fact that respiring bacteria in a biofilm on a metal use some of the oxygen which would otherwise be available to oxidize that metal. As noted above, however, this reduction of oxygen level also creates an opportunity for SRB, which are anaerobic, to colonize the metal. Thus, in practice, the effectiveness of biofilms as a means of inhibiting electrochemical corrosion is reduced by the consequent enhancement of the rate of SRB-related corrosion.

What is needed in the art is an effective and less expensive means to prevent or inhibit SRB-caused corrosion or degradation, with lessened release of toxic agents into the environment. The present invention provides these and other advantages.

SUMMARY OF THE INVENTION

The present invention relates to the field of corrosion prevention or inhibition through the use of bacteria which secrete antimicrobial chemical compositions. In particular, the invention relates to the use of bacteria which, either naturally or through the use of recombinant technology, secrete chemical compositions which inhibit the growth of sulfate-reducing bacteria on metals, concrete, mortar, and other surfaces subject to corrosion or degradation.

The invention provides for a method of inhibiting the growth of SRB on a corrosion or degradation sensitive material. The method comprises applying to the corrosion or degradation sensitive material a bacterium which secretes a chemical composition in an amount sufficient to inhibit the growth of SRB on the material. The corrosion sensitive material can be a metal, such as iron, aluminum, titanium, copper, or their alloys. For example, the metal can be mild steel or one of the various stainless steels. The degradation sensitive material can be a material such as concrete, reinforced concrete, or cement. The bacterium can be an aerobe, and can be, for example, of the genus *Pseudomonas*, or *Bacillus*. The chemical composition secreted by the bacterium can be one not normally secreted by a wild type member of the species of that bacterium and can be an antibiotic, such as gramicidin S, indolicidin, polymixin, or bactenecin, it can be a polyamino acid, such as polyaspartate or polyglutamate, or it can be a siderophore.

The invention further provides a system for inhibiting corrosion, comprising a corrosion or degradation sensitive material having a biofilm on its surface, wherein the biofilm includes a bacterium which secretes a chemical composition in an amount sufficient to inhibit the growth of SRB on the material. The corrosion sensitive material can be a metal, such as those set forth in the previous paragraph; the degradation sensitive material can be a material such as cement, concrete, or reinforced concrete. The bacteria can be an aerobe, particularly of the genus *Pseudomonas* or the genus *Bacillus*. The chemical composition secreted by the bacterium can be one not normally secreted by a wild type member of the species of that bacterium and can be an antibiotic, such as gramicidin S, indolicidin, polymixin, or bactenecin, it can be a polyamino acid, such as polyaspartate or polyglutamate, or it can be a siderophore.

S=Serine, and A=Alanine. Only relevant restriction sites are shown.

Figure 1A:
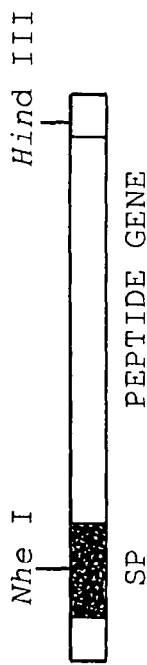
FIG. 1 Cloning and expression of indolicidin and bactenecin.

FIG. 1*a*: Schematic of expression system used for cloning and secreting indolicidin and bactenecin.

Figure 1B:
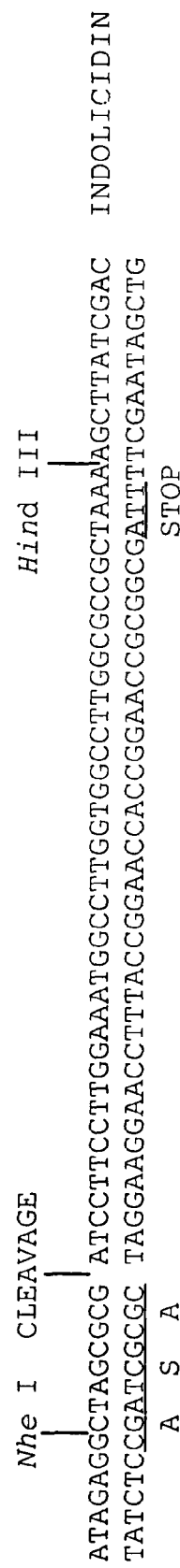

FIG. 1*b*: Complementary oligonucleotides used for cloning indolicidin (SEQ ID NO:1).

Figure 1C:
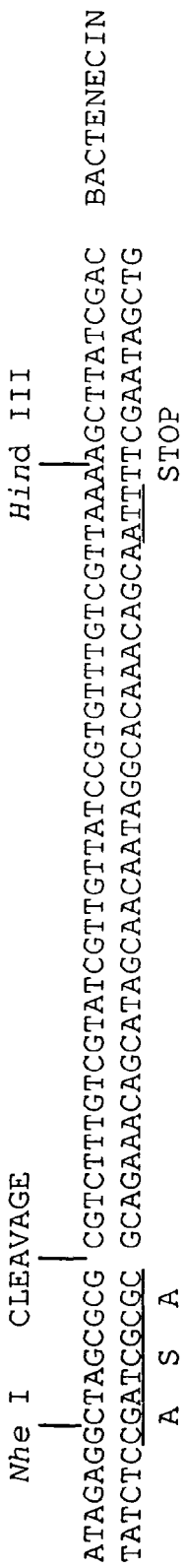

FIG. 1*c*: Complementary oligonucleotides used for cloning bactenecin (SEQ ID NO:2).

FIG. 2 Cloning and expression of bactenecin with a protective pro-barnase (pro) region.

Figure 2A:
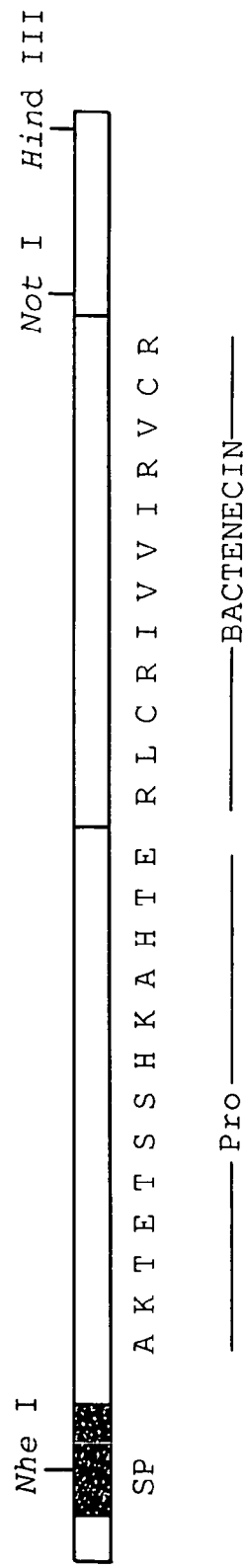

FIG. 2*a*: Schematic of expression system used for cloning and secreting pro-bactenecin. One-letter amino acid codes represent the pro-region and bactenecin peptide (SEQ ID NO:3). SP denotes the alkaline protease signal peptide.

Figure 2B:
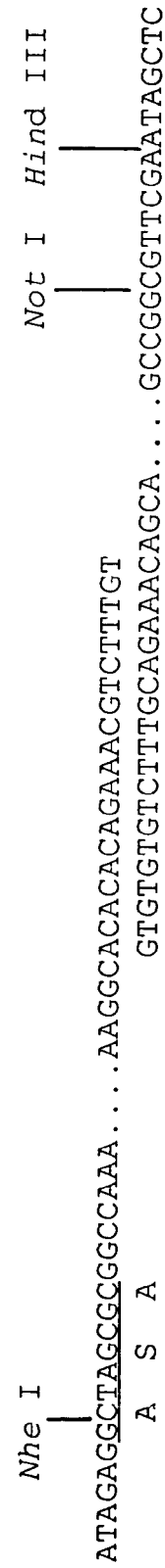

FIG. 2*b*: Relevant nucleotides for cloning pro-bactenecin (SEQ ID NOS:4–7). S=Serine, and A=Alanine. Only relevant restriction sites are shown.

FIG. 3 Impedance spectra of 304 stainless steel in modified Baar's's medium with dual cultures (except for control run) of *B. subtilis* BE1500 (with plasmid pBE92 in absence (hollow squares) and presence (filled squares) of SRB, pBE92-Ind (indolicidin) (filled diamonds), pBE92-Bac (Bactenecin) (hollow triangles), and pBE92-ProBac (bactenecin with a pro-region) (hollow circles)) and control bacteria *P. fragi* K (filled hexagons), and representative SRB *D. vulgaris*. Data are from a representative experiment.

Figure 3A:
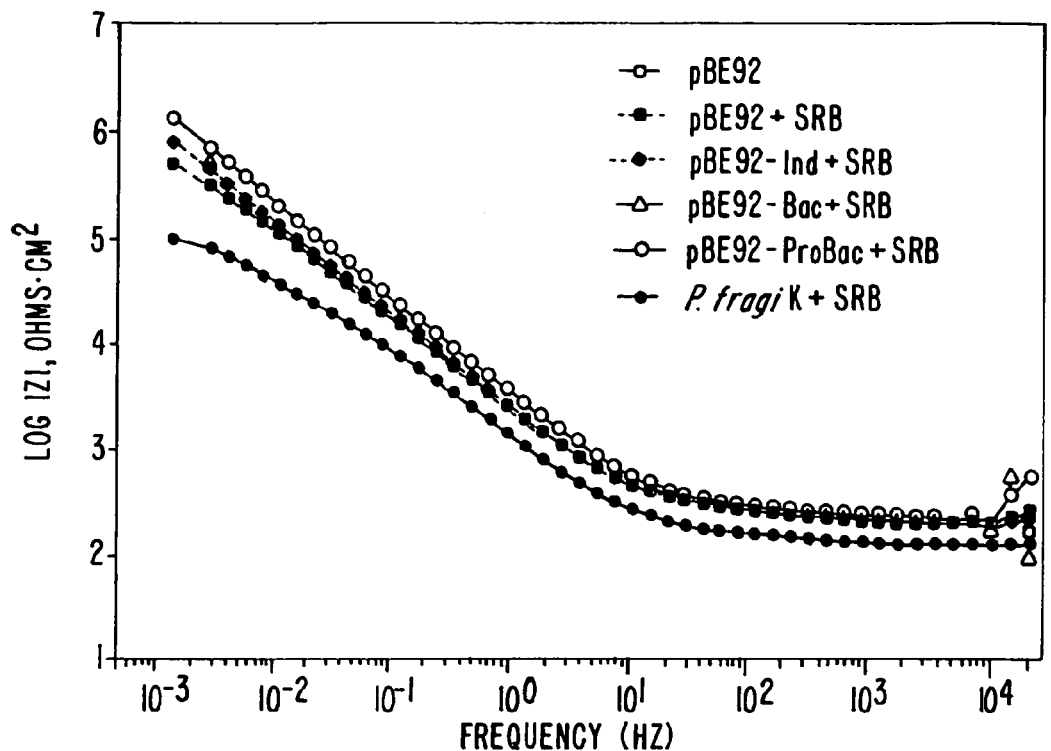

FIG. 3*a*: Y Axis: Log of the impedance. X Axis: Frequency in hertz.

Figure 3B:
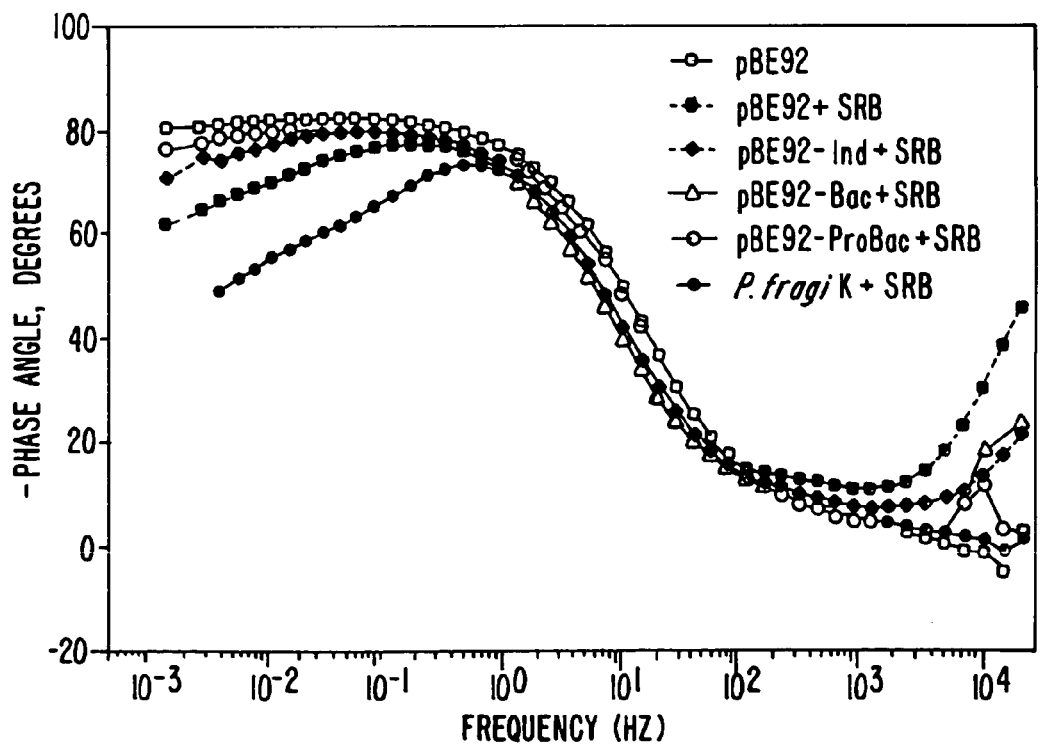

FIG. 3*b*: Y Axis:—Phase angle, in degrees. X Axis: Frequency in hertz.

A note on the interpretation of the impedance spectra set forth in FIGS. 3–9:

Electrochemical impedance spectroscopy is a technique in materials science that is used to investigate corrosion. The top graph in each of FIGS. 3–9 (the "a" figure) is a graph plotting the log of the impedance of the stated metal, treated as indicated for that figure, over a range of frequencies. The plateau in impedance at low frequencies is called the polarization resistance and is inversely related to the corrosion rate; thus, if the impedance at low frequencies goes up, it reflects that the corrosion rate has gone down. While the instrument sweeps through the range of frequencies shown in the graph, the portion of the graph considered relevant for corrosion studies is the result at the lowest frequency. Thus, the effect on the rate of corrosion of a change in the experiment is determined from the values graphed on the far left of the figure. Since the Y axis of the "a" graphs plots a number which is a log function, the difference between each number on the Y axis reflects a tenfold difference. Accordingly, small differences in the relative position of the data point for the respective lines reflect substantial differences in the rate of corrosion. More information about polarization resistance, impedance spectra, and other techniques to measure corrosion may be found in Baboian, R., ed., *Corrosion Tests and Standards: Application and Interpretation*, American Society for Testing and Materials, Philadelphia (1995).

The bottom graph in each Figure (the "b" figure) is a graph plotting the phase shift of the impedance response. These graphs confirm for each experiment that the impedance graphed in the "a" figure reflects a single time constant and that the plateau in impedance at low frequencies is the polarization resistance.

The X axis for all the graphs of FIGS. 3–9 (both "a" and "b") is the frequency in Hertz.

FIG. 4 Top and bottom panels: Impedance spectra of 304 stainless steel in modified Baar's medium with dual-cultures of *B. subtilis* WB600 (with plasmid pBE92, in absence (hollow squares) and presence (filled squares) of SRB, pBE92-Ind (indolicidin), filled diamonds, pBE92-Bac (bactenecin), hollow triangles, and pBE92-ProBac (bactenecin with a pro-region), hollow circles, and *P. fragi* K filled hexagons). "SRB" stands for the representative SRB *D. vulgaris*. Data are from one experiment.

Figure 4A:
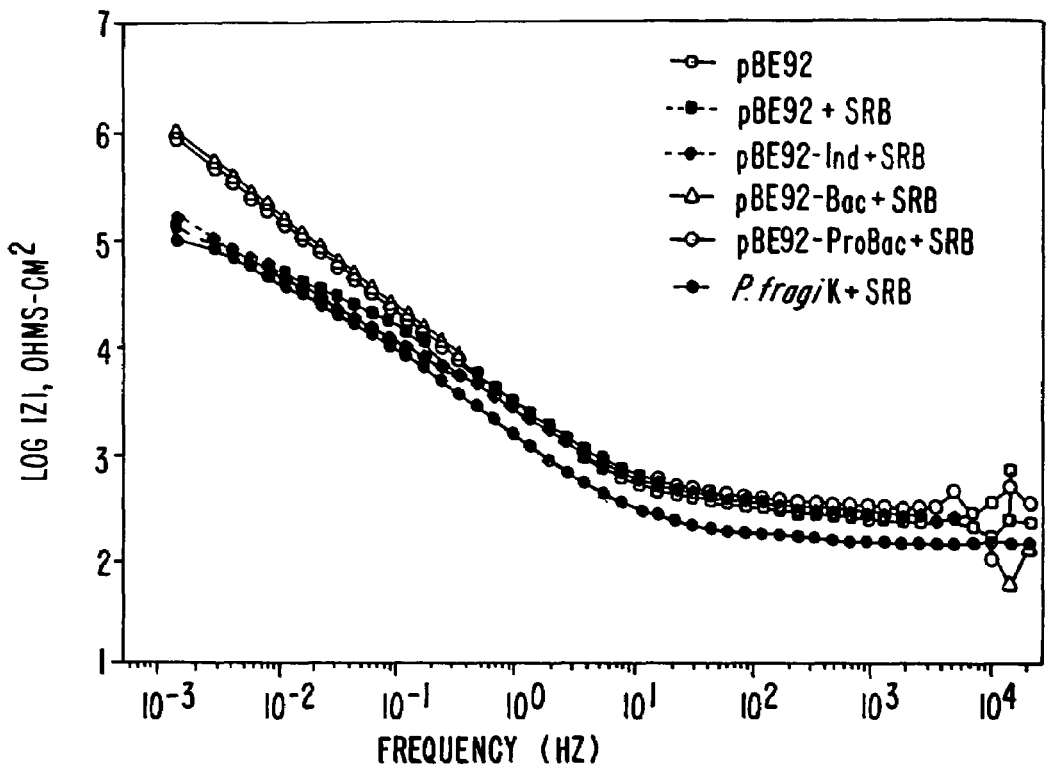

FIG. 4*a*: Y Axis: Log of the impedance. X Axis: Frequency in hertz.

Figure 4B:
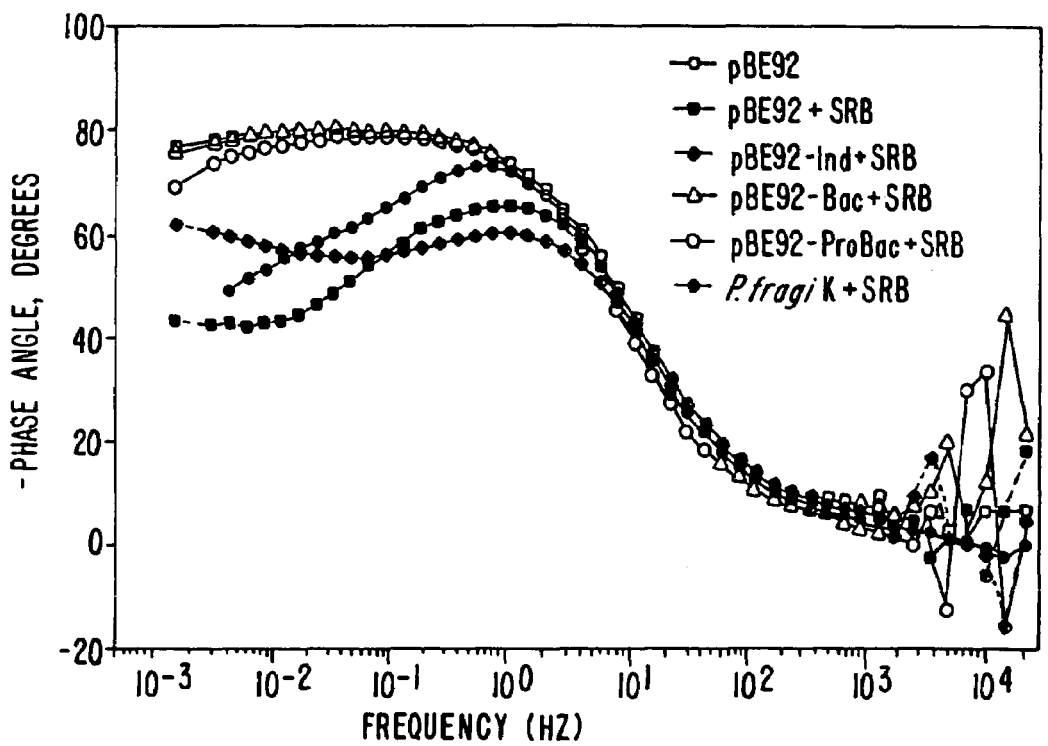

FIG. 4*b*: Y Axis:—Phase angle, in degrees. X Axis: Frequency in hertz.

FIG. 5 Top and bottom panels: Impedance spectra of 304 stainless steel in modified Baar's medium with dual-cultures of *B. polymyxa* (with plasmid pBE92 in absence (hollow triangles) and presence (filled circles) of SRB, pBE92-Bac (bactenecin) (hollow squares), and control bacterium *P. fragi* K (filled hexagons), with representative SRB *D. vulgaris*. Data are from a representative experiment (two independent experiments).

Figure 5A:
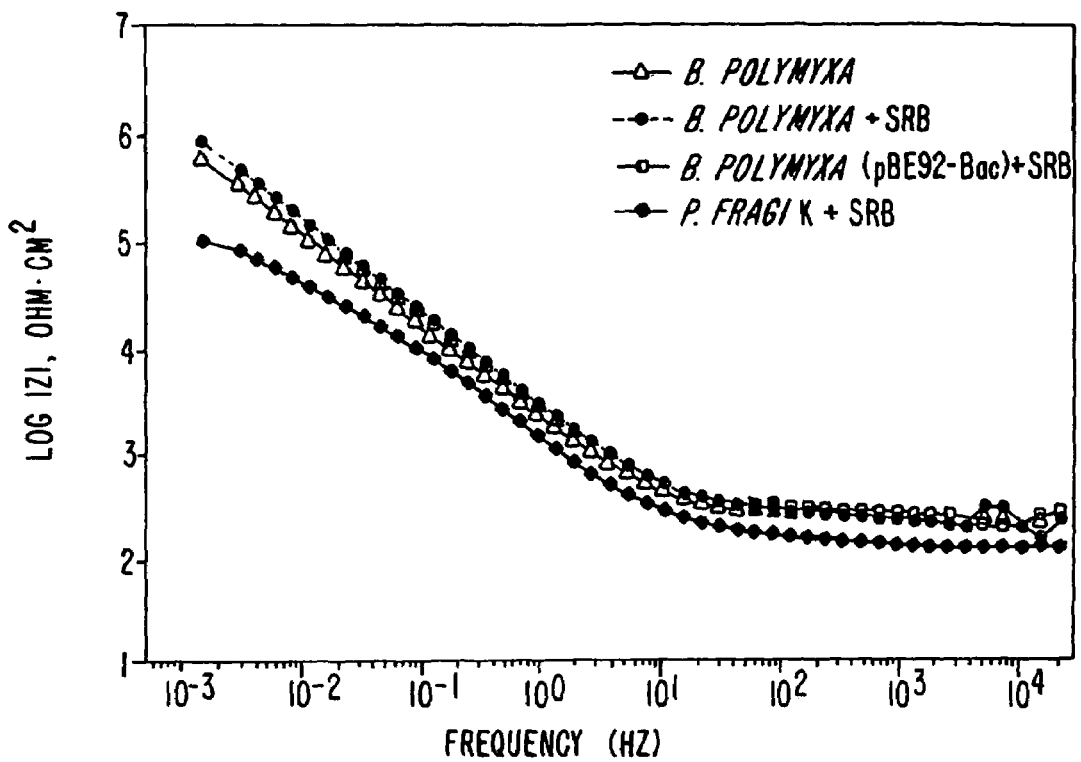

FIG. 5*a*: Y Axis: Log of the impedance. X Axis: Frequency in hertz.

Figure 5B:
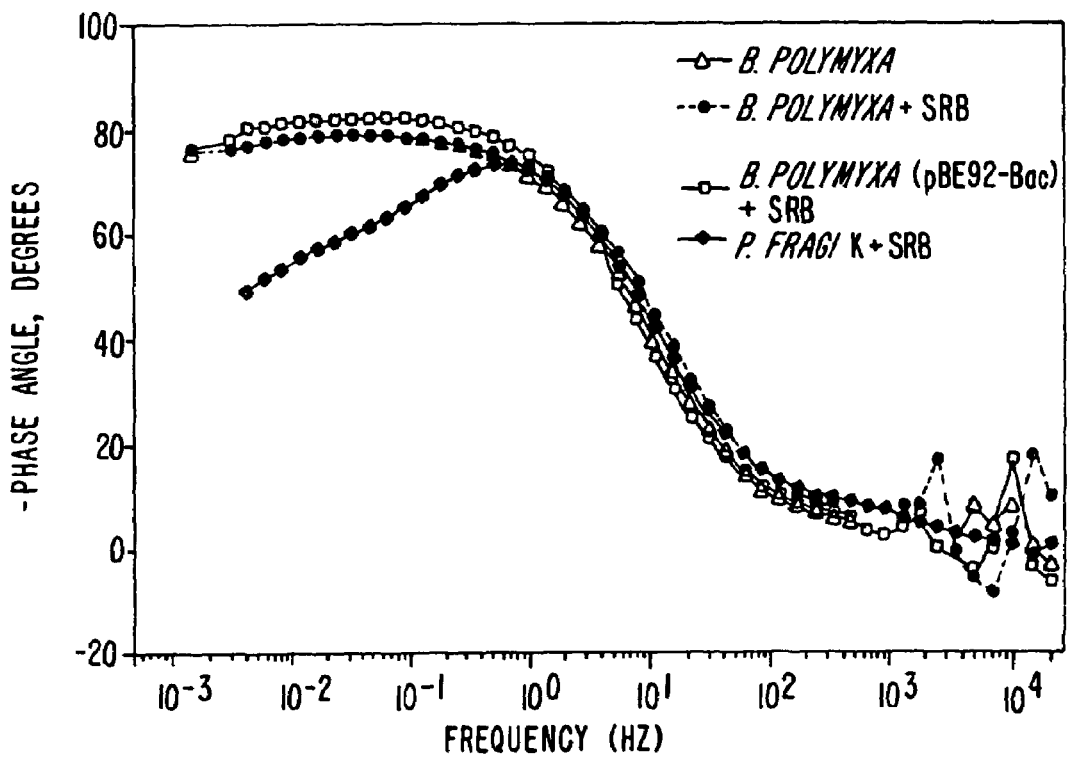

FIG. 5*b*: Y Axis:—Phase angle, in degrees. X Axis: Frequency in hertz.

FIG. 6 Top and bottom panels: Impedance spectra for SAE 1018 mild steel in modified Baar's medium with the purified antimicrobial ampicillin added to cultures of *P. fragi* K before and after SRB addition. Control culture of *P. fragi* K: hollow circles, *P. fragi* and SRB (*D. vulgaris*): filled diamond, *P. fragi* and SRB, with ampicillin added after SRB: filled triangles, *P. fragi* with ampicillin added before SRB: hollow squares. Data are from a representative experiment (from a minimum of two independent experiments).

Figure 6A:
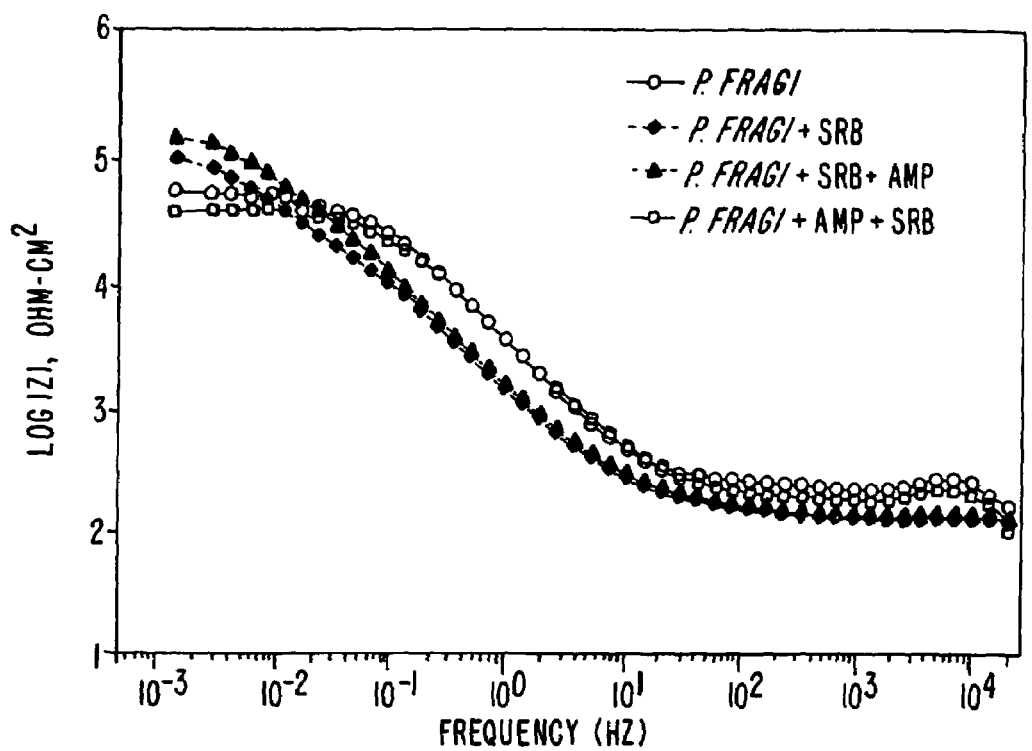

FIG. 6*a*: Y Axis: Log of the impedance. X Axis: Frequency in hertz.

Figure 6B:
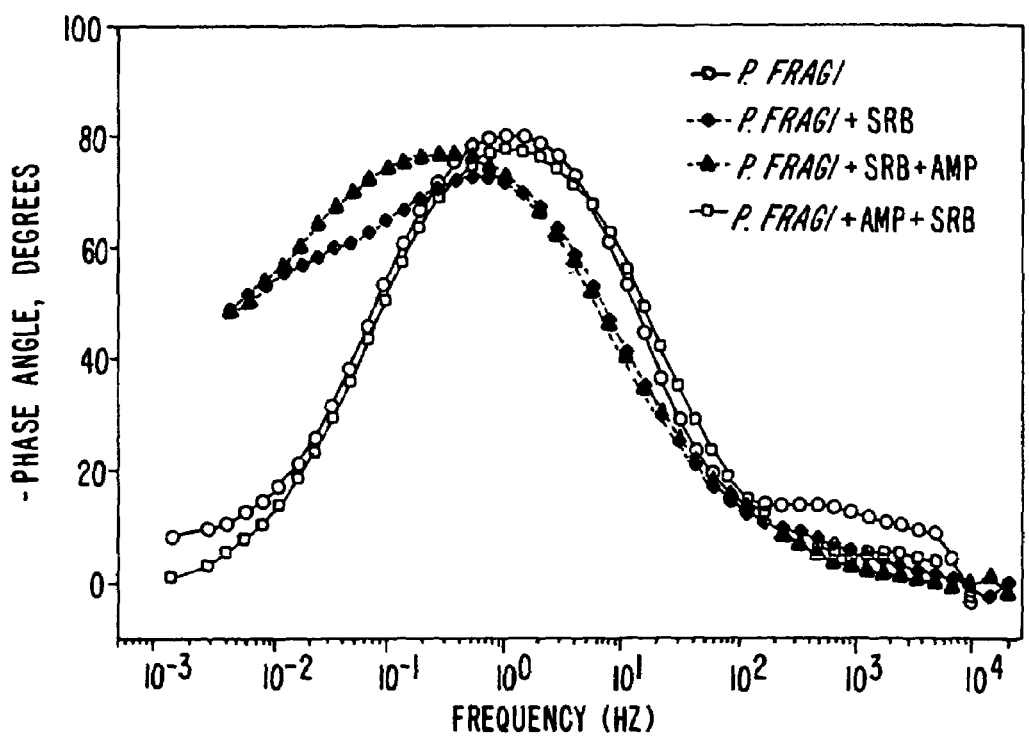

FIG. 6*b*: Y Axis:—Phase angle, in degrees. X Axis: Frequency in hertz.

FIG. 7 Top and bottom panels: Impedance spectra of 304 stainless steel in modified Baar's medium with the purified antimicrobial ampicillin added before and after SRB addition. Control culture of *P. fragi* K: hollow circles, *P. fragi* and SRB (*D. vulgaris*): filled diamond, *P. fragi* and SRB, with ampicillin added after SRB: filled triangles, *P. fragi* with ampicillin added before SRB: hollow diamonds. Data are from a representative experiment (minimum of two independent experiments).

Figure 7A:
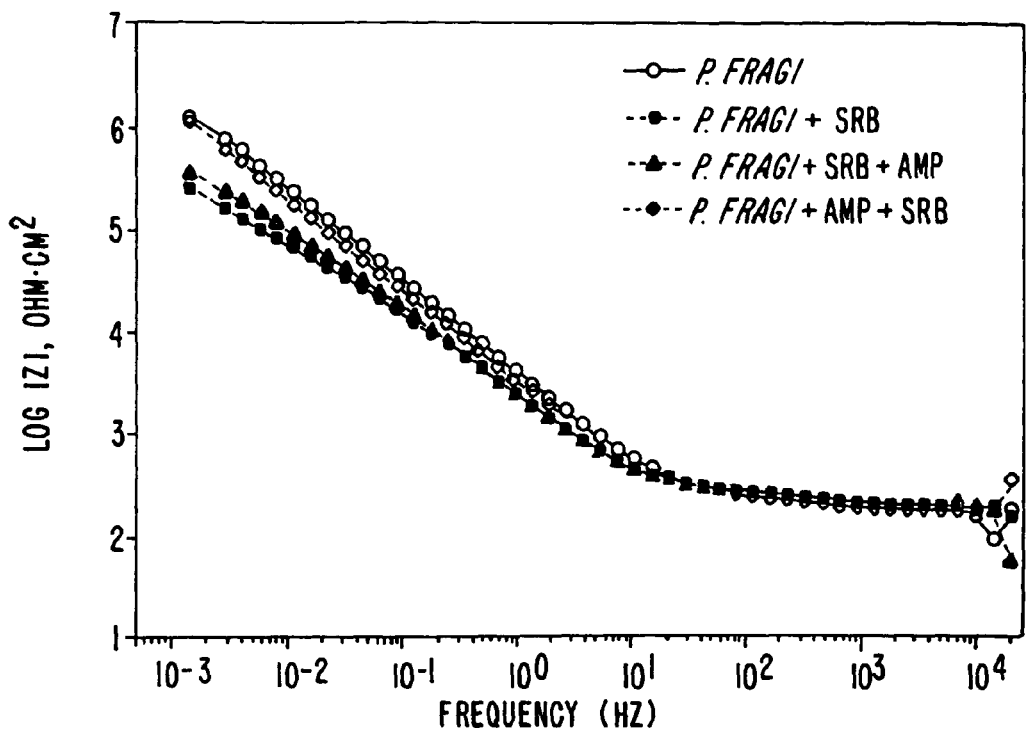

FIG. 7*a*: Y Axis: Log of the impedance. X Axis: Frequency in hertz.

Figure 7B:
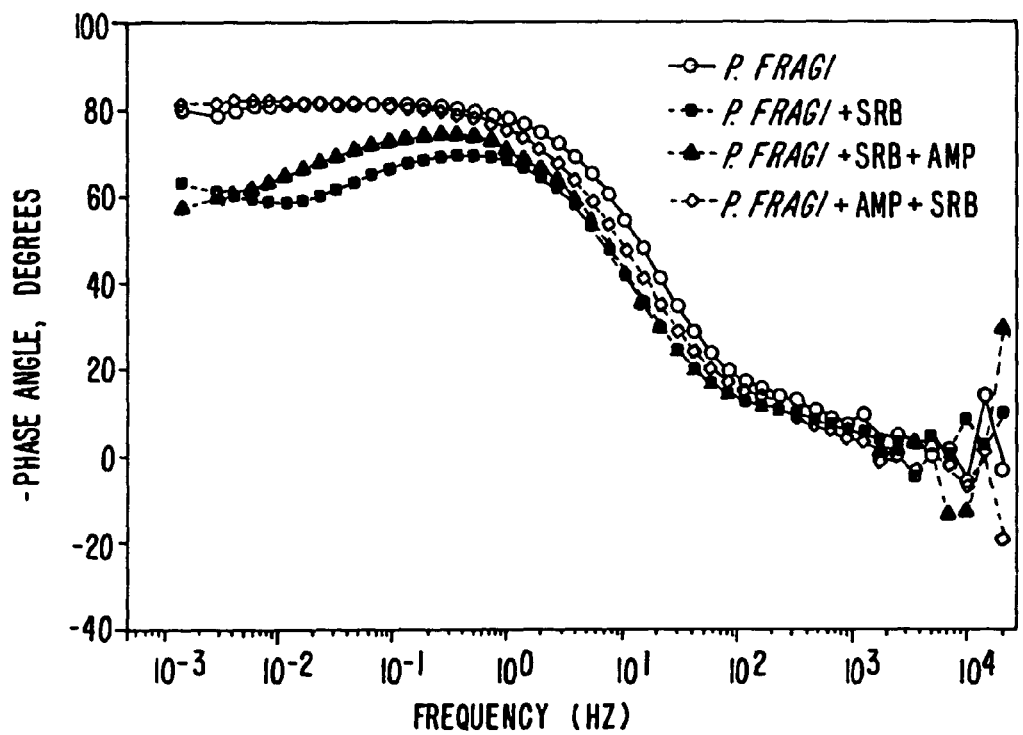

FIG. 7*b*: Y Axis:—Phase angle, in degrees. X Axis: Frequency in hertz.

FIG. 8 Top and bottom panels: Impedance spectra of 304 stainless steel in modified Baar's medium with the purified antimicrobial gramicidin S added before SRB addition and gramicidin S generated in situ by the recombinant biofilm.

Filled circles: control bacteria *P. fragi* and SRB; hollow diamonds: *P. fragi* and gramicidin S and SRB *D. vulgaris* (gramicidin S added before SRB); hollow squares: gramicidin S hyperproducing strain *B. brevis* 18; filled squares, *B. brevis* 18 and SRB. Data are from a representative experiment (minimum of two independent experiments).

Figure 8A:
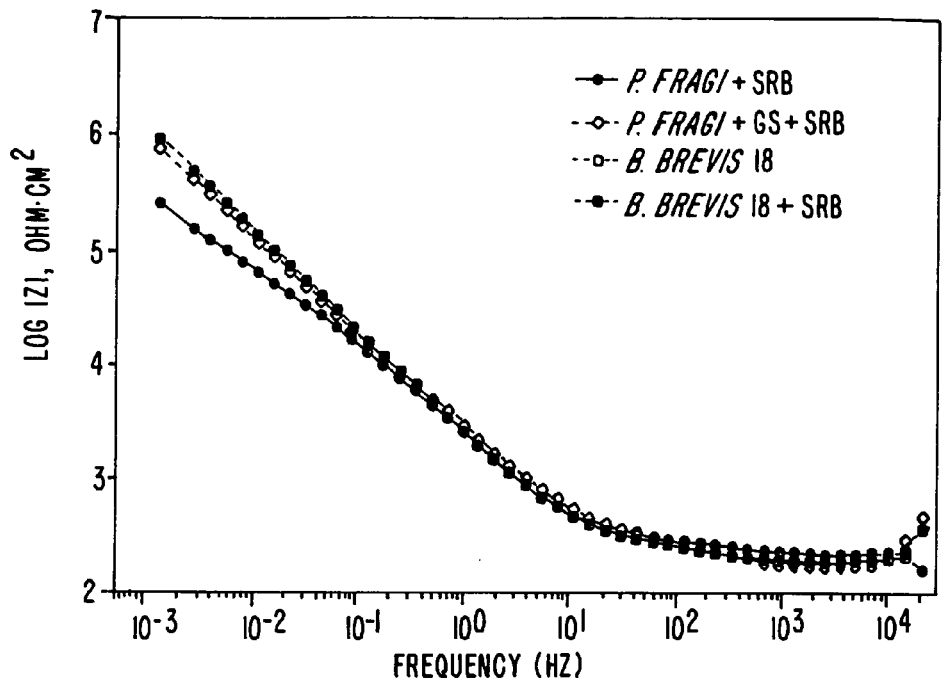

FIG. 8a: Y Axis: Log of the impedance. X Axis: Frequency in hertz.

Figure 8B:
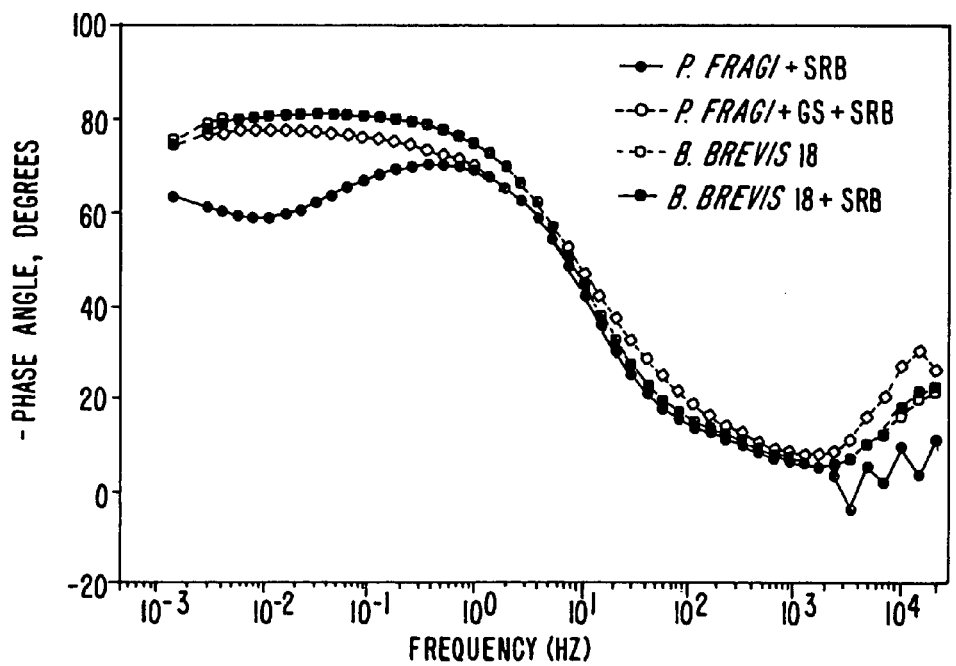

FIG. 8b: Y Axis:—Phase angle, in degrees. X Axis: Frequency in hertz.

FIG. 9 Top and bottom panels: Impedance spectra of SAE 1018 mild steel in modified Baar's medium with the purified antimicrobial gramicidin S added before SRB addition and gramicidin S generated in situ by the recombinant biofilm. Legend is as for FIG. 8. Data are from a representative experiment (minimum of two independent experiments).

Figure 9A:
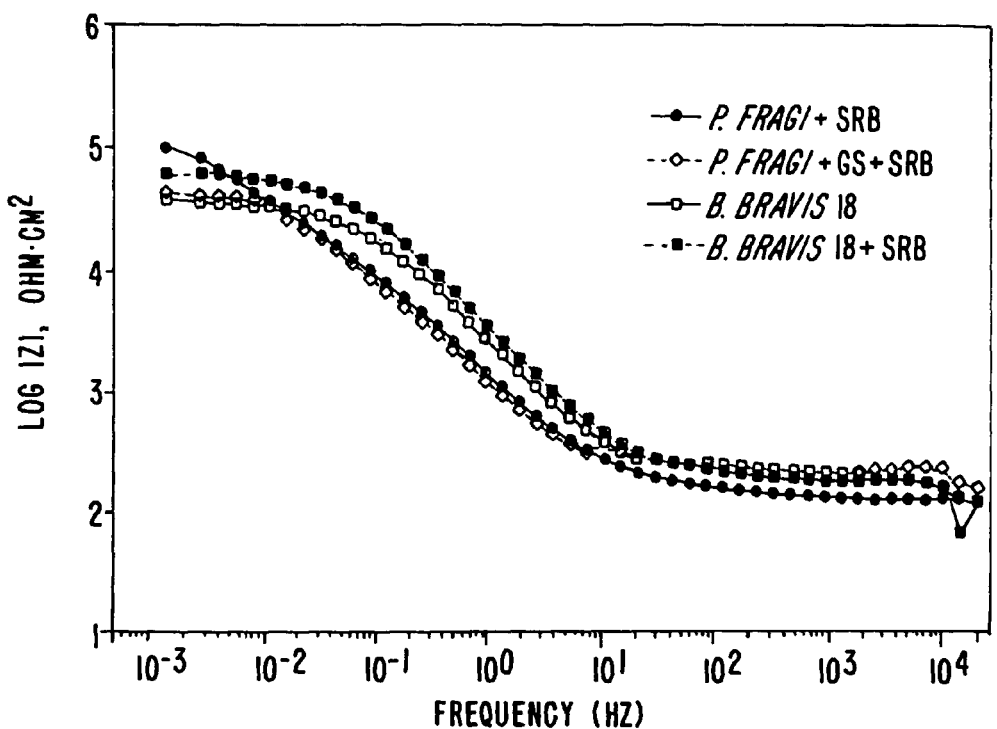

FIG. 9a: Y Axis: Log of the impedance. X Axis: Frequency in hertz.

Figure 9B:
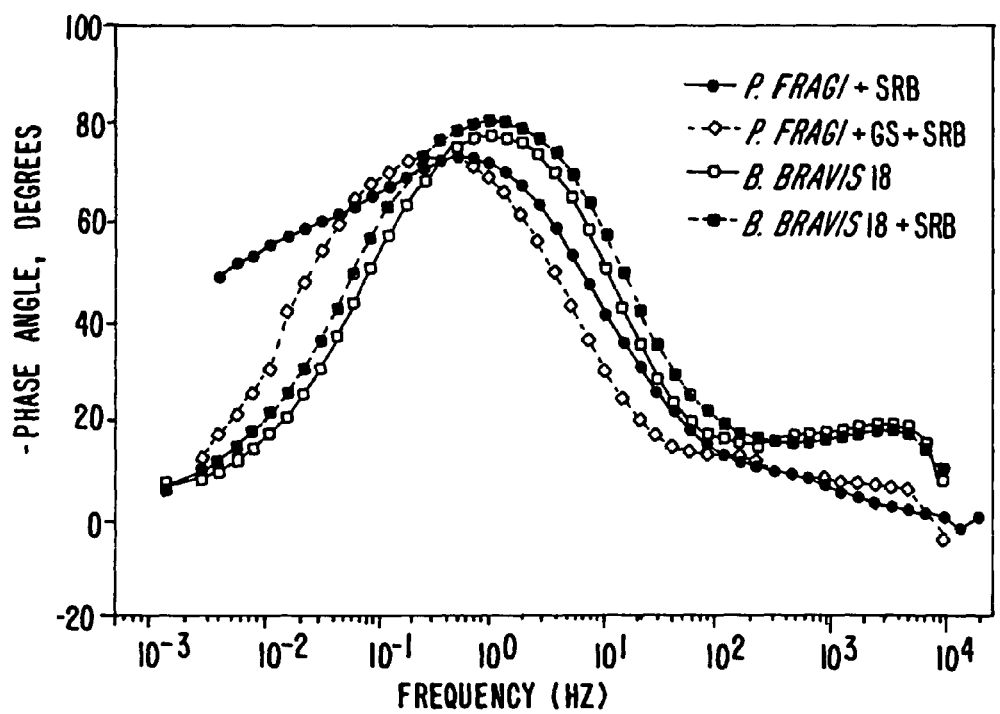

FIG. 9b: Y Axis:—Phase angle, in degrees. X Axis: Frequency in hertz.

DETAILED DESCRIPTION

I. Introduction

This invention provides methods of inhibiting degradation of materials, as well as a system for inhibiting degradation. We have recently shown that the presence of aerobic biofilms on metals can reduce corrosion by 2- to 40-fold. (Jayaraman et al., 1997a and Jayaraman et al., 1997b). This inhibition may be due in part to a reduction in oxygen levels at the surface of the metal due to bacterial respiration. In natural environments, however, this reduction in oxygen levels also creates an opportunity for colonization of the metal by sulfate-reducing bacteria, or "SRB." While the impact of SRB was not studied in Jayaraman et al., 1997a or 1997b, SRB would be expected to increase substantially the rate of corrosion over that reported in those studies. Accordingly, while the Jayaraman et al., 1997a and 1997b studies demonstrated that aerobic biofilms could serve as a means of inhibiting corrosion, they provided no guidance on how to reduce the impact of SRB mediated corrosion.

The present invention solves this problem. It therefore markedly increases the utility of aerobic biofilms as a means of inhibiting degradation. In brief, the invention involves the application of bacteria which secrete antimicrobial substances. We have now shown that it is possible to create biofilms of aerobic bacteria which secrete substances which inhibit SRB growth. The substances can be ones naturally secreted by wild-type bacteria not normally present in the biofilm into which the bacteria are introduced (including the secretion of substances at levels higher than normal due to mutation). The bacterium can also be recombinantly altered to overexpress a substance naturally secreted by the organism, or to secrete an antimicrobial not expressed by wild-type members of the bacterial species, or both.

Corrosion is a problem affecting metals. But other materials are seriously affected by degradation related to colonization of the material by SRB. SRB produce hydrogen sulfide as a product of their metabolism. Sulfide attacks iron, its alloys, including stainless steels, and oxidizes copper and its alloys. The hydrogen sulfide is available to be oxidized to sulfate by any of a number of sulfur-oxidizing organisms, such as *Thiobacillus*, which produce sulfuric acid. Sulfuric acid formed in this manner has been found responsible, for example, for the degradation of concrete water channels in Los Angeles and has dramatically reduced the expected service life of the concrete water control system.

While the invention is particularly useful against corrosion or degradation related to SRB, the method and system of the invention can also be applied to other organisms which increase corrosion or degradation of materials. For example, fungi such as *Hormoconis resinae* contaminate jet fuel and produce organic acids which increase the corrosion of aluminum alloys in the fuel system. See, e.g. H. A. Videla, Manual of Biocorrosion (CRC Lewis Pub., New York) (1996), at 129 (hereafter "the Manual;" the entirety of the Manual is hereby incorporated by reference). Use of bacteria secreting or engineered to secrete anti-fungals, or both, can reduce corrosion by this source. Similarly, growth of *Pseudomonas* in jet fuel enhances corrosion whereas *Serratia marcescens* was found to be protective. Id. at 129–132. The present invention would encompass the engineering of *S. marcescens* to secrete one or more antimicrobial substances inhibiting the growth of *Pseudomonas*, as well as SRB or other microbes which may be found to cause corrosion.

Inhibition of SRB-mediated corrosion or degradation, as well as of corrosion caused by other bacteria (such as *Pseudomonas*) or by fungi, by this method is highly desirable. Because bacteria reproduce themselves, the population of organisms secreting the antimicrobial agent replenishes itself over time. Thus, a single application can be effective over a long period, in contrast to the application of organic or inorganic chemicals, which must usually be frequently repeated. Moreover, the secretion of the agent in the biofilm itself automatically places the highest concentration of the agent at its point of action, unlike exogenously applied chemicals, which are typically applied in large quantities to ensure an adequate dose reaches the SRB or other intended target organism. Further, the mechanism by which SRB obtain energy is only slightly energetically favored and the growth of the organisms can be inhibited by agents which will not seriously affect other organisms. Thus, the secretions of antimicrobial agents by surrounding microbes can completely inhibit or reduce the resistance of SRB to other agents, rendering it possible to inhibit SRB-related corrosion or degradation by the exogenous application of biocides and other toxic agents at much lower levels than those which would otherwise be required.

An additional advantage of the invention is that even if the biofilm is damaged or removed in a few places due to fluid flow or abrasion, the continuous supply of inhibitor from the neighboring regions would preferentially favor the recolonization of the exposed metal or other surface by the inhibitor-producing bacteria. Since biofilms can form rapidly on exposed surfaces (Costerton, 1995), the judicious choice of bacterium can result in the exclusion of other bacterial species from the biofilm.

Finally, the degradation or corrosion inhibitory effect of a biofilm can be further enhanced by introducing bacteria which secrete degradation or corrosion-inhibitory agents, either separately or in combination with antimicrobial agents. Such degradation or corrosion inhibitory agents can include polypeptides such as polyaspartate and polyglutamate, as well as siderophores such as parabactin and enterobactin.

The following text sets forth some of the many uses for the invention, and how to practice it. After defining terms, the text discusses the enhancement of the anticorrosive effect of an aerobic biofilm by the use of organisms secreting anti-SRB or anti-fungal agents, including both organisms which naturally secrete such agents and those which are genetically engineered to do so. In addition, it describes the use of anti-corrosion or anti-degradation agents such as polypeptides and siderophores to further enhance the anti-corrosion effect. The text further describes how to choose an appropriate organism for use in the method or the system of the invention and how to determine if the organism produces (before or after alteration) substances which inhibit the growth of the SRB, fungus, or other target organism. It then discusses methods for applying the organisms before or after the material to be protected is placed into service, and describes uses for the method and for the system. Finally, it sets forth examples.

II. Definitions

As used herein, "mild steel" refers to an inexpensive, low grade steel commonly used for piping and the like. "SAE 1018 steel" is a particular grade of mild steel which meets an industry standard set by the Society of Automotive Engineers.

As used herein, "stainless steel 304" or "304 stainless steel" refer to a particular grade of stainless steel meeting the industry standard for that designation.

The term "metal coupon" refers to a small, thin rectangle or circle of metal. Such "coupons" are routinely used in the art for comparing corrosion characteristics of different metals, agents, and inhibitors.

As used herein, "corrosion sensitive material" includes all metals subject to corrosion, specifically including iron, aluminum, titanium, copper, nickel, and alloys of each of these, including mild steel and stainless steels.

"Corrosion" applies specifically to damage to metals, while "degradation" refers to damage of other materials, such as concrete, cement, mortar and like materials. Thus, as used herein, a "degradation sensitive material" is a non-metal subject to damage from bacterial-related causes. For convenience of reference, however, as used herein, the term "corrosion" can also encompass damage to materials other than metals, unless otherwise required by context. Dental implants can also be a "degradation sensitive material."

As used herein, "chemical composition" means a chemical which has a growth inhibitory effect on a microorganism which can cause corrosion of metal or degradation of a non-metallic material. The term is generally but not necessarily used herein synonymously with the term "antimicrobial agent."

The term "applying" is intended to encompass any means mediated or facilitated by human action by which bacteria come into contact with the surface includes, as appropriate in the context, contacting, spraying, brushing, hosing, or dripping bacteria or a mixture containing bacteria onto the corrosion or degradation sensitive material. It also comprehends including bacteria secreting an antimicrobial composition, such as an anti-SRB composition, in an initial bolus of water run through, for example, a pipe, conduit, cooling tower or water system, when the pipe, conduit, tower, or system is first placed in service. It is further intended to comprehend the physical placement of bacteria on a surface, with or without scraping of the surface to create a space within an existing biofilm.

The phrase "in an amount sufficient to inhibit the growth of sulfate-reducing bacteria" means an amount sufficient to reduce the growth of such bacteria in a statistically significant manner in comparison to a control population. The range can be as low as the limit of the ability to detect a statistically significant difference up to complete inhibition. Preferably, the degree of inhibition is at least about 10%, meaning that the growth of such bacteria is at least about 10% less than the growth of the control population. More preferably, the degree of inhibition is about 30–50%. Even more preferably, the degree of inhibition is about 50–90%. Most preferably, the degree of inhibition is 90% or greater.

III. Enhancing the Anti-corrosion Effects of Biofilms

A. Enhancement of the Anticorrosive Effect of Biofilm by Bacteria Secreting Antimicrobials 1. General Surfaces exposed to natural environments rapidly become colonized by aerobic bacteria. Metals and other surfaces develop adherent microbial populations enclosed in a polysaccharide coating known as a glycocalyx (Costerton, 1995). As noted in the Background, recent work by the inventors has confirmed that biofilms have a protective effect on surfaces when grown as a mono- (or "axenic") culture. In nature, however, organisms rarely grow in monocultures and the anoxic regions found near the surface of the metal or other material due to the depletion of oxygen by the aerobic bacteria in the biofilm creates an opportunity for colonization of the material by sulfate-reducing bacteria, or "SRB." These bacteria are thus responsible for corrosion even in an aerobic environment. (Hamilton, 1990).

The protective effects of the biofilm can be enhanced by introducing into an existing biofilm one or more bacteria which secrete antimicrobial agents which inhibit the growth of SRB. In one embodiment, the bacteria can be of a kind which, either ordinarily or as the result of a mutation, naturally produce and secrete an agent which inhibits SRB growth. Alternatively, the bacteria can be altered through recombinant technology, either to secrete antimicrobial agents not secreted by unaltered members of their species, or to secrete at higher levels or continuously an agent they would normally secrete at lower levels or only at certain times.

2. Natural Bacterial Secretors

Some bacteria naturally produce agents which are effective in inhibiting the growth of microbes, such as SRB, which cause corrosion. The biology of bacteria has been studied for decades and a considerable body of knowledge has developed, including information regarding a number of bacteria which are known to secrete antimicrobial agents. One such bacterium, which over-expresses the anti-bacterial agent Gramicidin-S as the result of an induced mutation, is described further and tested for its ability to inhibit SRB-mediated corrosion in the Examples, below (bacteria which overexpress an agent as the result of a chemical mutation are considered to be natural secretors of the agent for present purposes). Other bacteria known to secrete antimicrobial agents can be easily tested to determine the effectiveness of their secretions against microorganisms, such as SRB or the fungus *Hormoconis resinae*, which cause corrosion according to assays taught in the Examples below, or as known in the art.

3. Recombinantly Altered Secretors a) Chemicals not Naturally Produced by the Bacterium to be Used as a Secretor It will not always be the case that a bacterium naturally secreting a particular antimicrobial can be found, or that the bacteria which naturally secrete the antimicrobial desired for a particular application would thrive in the particular environment to which it would be exposed. In these and other instances, a bacterium which does not naturally secrete the antimicrobial agent in question can be altered by recombinant biology techniques to secrete the desired antimicrobial agent.

b) Chemicals Naturally Produced by the Bacterium, But in Larger Quantities or Constitutively Recombinant techniques can also be used to improve the anti-SRB corrosion properties of bacteria which do normally secrete antimicrobial agents by transfecting them with constructs which include the gene for the agent operably linked to a strong constitutive promoter to increase the amount of the agent secreted, or to provide continuous production of an agent normally produced discontinuously or only in response to particular environmental or metabolic conditions. The construct may alteratively place the gene encoding the antimicrobial agent under the control of an inducible promoter so that the secretion of the agent can be controlled.

c) Introduction of DNA Constructs into Bacterial Cells

It will be appreciated that a number of techniques are known in the art for introducing DNA, including heterologous DNA, into bacterial cells. An exemplar method for doing so is set forth in the Examples, below. The choice of the particular method for introducing such DNA into bacteria and obtaining its expression is not critical to the practice of this invention.

B. Choice of Antimicrobial Composition

1. Antimicrobial Agents

A number of antimicrobial agents which can be produced by bacteria are known in the art. Nisin, for example, a 34 amino acid peptide secreted by the bacterium *Lactococcus lactis*, is used as a food preservative. A 1700 amino acid polypeptide secreted by the marine bacterium known as D2 has been shown to have general antimicrobial activity. Any of these antimicrobial agents which are inhibitory of the target organism or organisms, such as SRB, may be used in the invention.

In a preferred embodiment, the antimicrobial agent is a peptide antibiotic. Peptide antimicrobial agents can be small (typically 10–35 amino acids), and small ones may be cloned into bacteria more readily than many conventional antibiotics, for which large operons or several pathways may be needed to achieve the expression of a single antibiotic. In addition to those mentioned above, a number of peptide antibiotics, such as Gramicidin S and D (discussed in the Examples, below), are known in the art. Larger antibiotic compositions may, however, be used if desired for the particular application in question so long as they may be expressed in bacteria in sufficient quantities.

Other small peptides, not normally considered as antibiotics but which have antimicrobial effects, may also be used. For example, indolicidin and bactenecin are cationic antimicrobial peptides from bovine neutrophils known to be active against a wide range of organisms (detailed information about these compounds, including references to the literature, are set forth in the Examples, below). Indolicidin is the smallest known linear antimicrobial peptide.

The choice of the particular antimicrobial chemical is within the judicious discretion of the practitioner and will depend on the target organism, the organism chosen to secrete the antimicrobial, and the application in which the secreting organism is to be employed. The antimicrobial chosen should be inhibitory to the target organism (for example, it should inhibit fungal growth if the target is a fungus, *Pseudomonas* growth if the target organism is a pseudomonad, and so forth. Exemplar assays for determining the inhibitory effect of antimicrobials on members of a group of organisms are taught in the Examples). In order to permit the continued production of the antimicrobial over time, the antimicrobial chosen will typically be more inhibitory to the target organism than to the organism secreting the antimicrobial (sometimes referred to as the "host organism," if the organism is expressing an introduced gene). An exemplar assay for determining the sensitivity of the host organism to an antimicrobial is set forth in the Examples. Under some circumstances, however, continued production of the antimicrobial may not be necessary, no other organism may be available which can secrete a particular antimicrobial, or it may be desirable to eliminate the producing species at about the same time as the target species is eliminated or inhibited. In these situations, an antimicrobial may be chosen which will be inhibitory to the host organism as well as to the target organism.

Finally, the choice of the antimicrobial will depend in part on the intended application. Indolicidin and bactenecin, for example are antimicrobial agents derived from bovine neutrophils. Their release into the environment might therefore result in the development of bacterial strains resistant to these natural antimicrobials of at least the bovine immune system, and could possibly result in the development of strains more resistant to similar antimicrobial agents in the human immune system. For this reason, indolicidin and bactenecin are not preferred antimicrobials for use in open systems (that is, systems where the secreting organisms or the secreted antimicrobials are typically released in to the environment, such as water conduits, drainage pipes, and the like). On the other hand, these compounds can be used in closed systems, that is, where the organisms and the secreted antimicrobials will not typically be released into the environment.

2. Anticorrosive Agents a) Polypeptides

Amino acids, and especially glycine, aspartic acid and glutamic acid, are known to act as corrosion inhibitors. See, e.g., Kalota and Silverman, *Corrosion* 50(2):138–145 (1994) (hereafter, Kalota and Silverman) and references cited therein. Many amino acids, however, tend to have more than one acid-base constant, with multiple pK values, and different charges, depending on the pH of their environment. Kalota and Silverman found that the ability of amino acids of low molecular weight to inhibit corrosion depended on the pH, and that only at high pH (pH≧10) was the corrosion rate reduced significantly.

Based on Kalota and Silverman, it would be desirable to engineer the bacteria to secrete polyaspartate, polyglutamate, or polyglycine, or polypeptides consisting of these three amino acids, as corrosion inhibitors only for use in environments in which the pH would be about 10 or higher. While this would apply to some industrial uses, the number of situations involving such high pH is likely to be somewhat limited.

Our own studies contradict Kalota and Silverman. We have found that polyaspartate and polyglutamate, for example, protect metal from corrosion at pHs as low as 7. According to our data, therefore, corrosion inhibition is possible if bacteria secrete polypeptides, such as polyaspartate, polyglutamate (or of their corresponding acids or salts), polyglycine, or mixtures of these amino acids, if the expected or measured pH of the environment of the metal is about 7 or higher. Accordingly, it will enhance the corrosion inhibitory effect of an aerobic biofilm if organisms in the biofilm secrete these polypeptides when the pH is about 7 or higher.

b) Siderophores

Siderophores such as parabactin (isolated from *Paracoccus denitrificans*) and enterobactin (isolated from *E. coli*) are relatively low molecular weight chelators generated and secreted by bacteria to solubilize ferric ions for transport into their cells. (McCafferty and McArdle, *J. Electrochem.*

Soc., 142:1447–1453 (1995)). These agents have been tested and found to inhibit corrosion of iron. Id. To enhance the anti-corrosive effect of a biofilm, the genes for these agents can be placed under the control of a strong constitutive promoter and expressed at levels higher than normal, or inserted into bacteria which do not normally secrete them.

3. Combinations of Antimicrobials, Anticorrosives, or Both

It is contemplated that a bacteria used in the invention may be designed to secrete more than one antimicrobial agent. One of the studies reported in the Examples, for instance, involved the use of a *Bacillus* which overexpresses Gramicidin S as a result of a mutation, and which was also genetically altered to produce another antimicrobial agent. Use of bacteria secreting two or more antimicrobials is likely to be advantageous as it renders it more difficult for the target corrosion-causing organism (be it an SRB or a fungus) to develop resistance.

Additionally, a bacterium which secretes an antimicrobial agent may have its ability to inhibit corrosion enhanced by being engineered to also produce an anti-corrosive agent, such as polyaspartate, polyglutamate, polypeptides consisting of these two peptides, or parabactin, enterobactin, or another siderophore. As a practical matter, the limitation on the number of antimicrobial and anticorrosive agents the bacterium can be engineered to produce is likely to be a combination of any toxic effects of the antimicrobial agents on the host cell and of the metabolic drain on the host cell of producing the substances secreted. Since different organisms have different metabolic efficiencies, and since the nutrient availability in the environment is likely to have a role, the determination of how many agents the chosen bacteria will be able to secrete will usually be determined empirically. Such determinations can be easily performed by serially transforming the bacteria with the desired antimicrobial and anticorrosive agents, in a medium containing the nutrients expected for the site of intended use, until a point is reached at which the target cells are completely inhibited, and then choosing the best combination of (1) the competitiveness of the host cells in relation to the natural population of the biofilm and (2) the ability of the host cells to secrete a desired number of agents.

C. Determination of an Appropriate Organism for the Intended use

1. Selection of Bacteria Exogenous to the Environment of the Intended use

In general, organisms will be selected to secrete antimicrobial agents against SRB, fungi, or other target microbes, according to the intended use. Our findings indicate that aerobic bacteria protect surfaces from corrosion and degradation; accordingly, the organism chosen should be aerobic. Further, the organism must be capable of living in the environment of the intended use. If, for example, the object is to protect steel and concrete of a bridge anchored in and arching over sea water, an organism capable of growing in sea water or salt spray should be chosen. Conversely, if the intention is to protect pipes or conduits which carry fresh water containing industrial waste, than the organism should be able to grow in fresh water and the presence of the expected effluents. Additionally, the organism should be able to grow under the expected temperature and pH conditions of the intended environment. Since bacteria have been studied intently for almost a hundred years, the temperature, pH and other environmental needs and tolerances of most species are known and available in the literature.

Preferably, the organism should be able to exert a protective effect against corrosion under the anticipated environmental conditions. We have published the results of a study in which we compared the effects of 15 different bacteria representing 7 different genera in protecting metal in two different media, one mimicking sea water and one a freshwater medium richly laced with nutrients. Jayaraman et al., Appl. Microbiol. Biotechnol., 48:11–17 (1997c) (hereafter, Jayaraman et al., 1997c; the entirety of this reference is incorporated by reference). The extent of corrosion inhibition varied markedly between the two media for some of the bacteria, while 10 of the organisms tested protected the metal notably well in both media. Id., at 397. Following the assays of this study, one of skill in the art can easily determine whether any particular bacterial species contemplated for use in the present inventive method or as part of the present inventive system will be able to grow in the medium presented by the intended environment and whether the organism will be protective against corrosion under those conditions.

In addition, it is preferable if the organism is capable of growing in a biofilm. Often these are organisms which are capable of "sliming." Exemplar genuses are *Bacillus, Pseudomonas, Serratia*, and *Escherichia* (although *Pseudomonas* species should not be chosen for use in those environments, such as aviation fuel tanks, where those organisms have been found to cause corrosion. See, e.g., the Manual, supra, at 129.) An exemplar method for determining the ability of selected organisms to form biofilms is taught in Jayaraman et al., 1997c, supra.

2. Selection of Bacteria Endogenous to the Environment of the Intended use

A preferred means of selecting appropriate bacteria in connection with installations already in use is to let nature do it. Since biofilms are pervasive in nature, pipes, conduits, water cooling towers, power plant reservoirs and similar equipment and installations will likely have biofilms already present, consisting of organisms already naturally selected for their ability to grow in that environment. A sample of these organisms can be removed (for example, by scraping the biofilm), cultured by standard techniques, and identified. If the species identified are otherwise suitable (they are, for example, convenient to modify genetically, and are not known to enhance rather than to inhibit corrosion), they may themselves be modified to secrete the desired antimicrobial agent. If desired, however, pure cultures of the organisms found at the site may also be purchased or grown from stock rather than using cultures grown from the organisms found at the site.

Once the organisms have been modified to secrete the antimicrobial agent selected, they can be introduced into the conduit, pipe, tower, or other installation. Introduction into the installation can be by any convenient means, such as by scraping the surface at intervals to provide a break in the biofilm and pipetting an aliquot of the culture onto the site scraped. In a preferred method, the bacteria are introduced by simply allowing a "plug" of water (that is, a bolus of water) containing a high concentration of bacteria to pass over the material to be protected. The bacteria will adhere to the biofilm throughout the course traversed by the water and become an intergral part of the biofilm, or form one if one is not already present.

D. Methods of Application

1. Application of Organisms Prior to First Entry of the Installation into Service Our research has shown that the reduction of SRB-related degradation of a surface is more successful when colonization of the surface by the SRB is prevented, rather than attempting to remove colonization which has already occurred. Accordingly, a preferred method of practicing the invention is to treat a corrosion or degradation sensitive material with bacteria secreting appropriate antimicrobial agents, such as one suitable for inhibiting the growth of SRB, before the equipment, system or installation is placed into service.

If the bacterium chosen is a spore-former, the organism can be cultured under conditions causing spore formation, the spores applied to the dry surface of the installation prior to use, and the surface wetted to activate the spores just before the entry of the installation into service. If the bacterium is not a spore former, or if it is not convenient to first have a spore-forming bacterium form spores, due, for example, to time constraints, media containing the bacteria may be applied to the surface by any convenient means, such as brushing, spraying, aerosoling, pipetting, hosing, or dripping the culture onto the surface.

If the surface is irregular or has nooks and crannies, then spraying or aerosoling the surface will be preferable as they permit better inoculation of the nooks and crannies. Some installations, such as outside fountains, water cooling towers, heating and cooling systems, and the like, are designed to recirculate water, oil, or other liquids through the system. Such installations may conveniently be inoculated by first inoculating a bolus of water which is then used to charge or flush the system. Other systems, such as pipes, which are open or which otherwise do not recirculate liquid placed in the system, may also be inoculated in this manner.

2. Application of Organisms after an Installation is in Service

The elimination of SRB once they are established in a biofilm is difficult. In some circumstances, it may be possible to disassemble all or part of an apparatus, equipment or installation, and to sterilize all or part of the surface with, for example, concentrated biocides or "live" steam. In other situations, it is possible that installations which cannot be disassembled can be flushed with strong biocides or live steam to kill the biofilm. Installations so treated can be inoculated by the same means as described in the preceding section for treatment prior to use.

For installations which cannot be so treated, or in which the biofilm cannot effectively be removed, the existing biofilm can be used to advantage by modifying the organisms already present to secrete the desired antimicrobials, as described above. The bacteria secreting the desired agents can then be reintroduced into the biofilm. If desired, the organisms can simply be introduced into the liquid or other media, or brushed or sprayed onto the surface. The bacteria may be more successfully introduced by scraping or otherwise disrupting the biofilm before introducing the new bacteria to create a space in which they can establish themselves.

E. Uses of the Invention

1. Closed Systems

There are a large number of closed systems (that is, systems which do not routinely discharge their contents into the environment) in use in industrial, commercial and utility settings. Examples include steel storage vessels, which are commonly pressure tested on site and then used to store liquids for extended periods, water cooling towers, used both in power plants and in the heating and cooling plants of plants, office buildings, and other commercial buildings, heat exchangers (which have been known to fail due to SRB related corrosion), and fire protection systems. These systems typically employ metal pipes and storage containers. Aerobic bacteria secreting appropriate antimicrobial agents, or anti-corrosion agents, or both, can be used in these settings to form a biofilm with enhanced ability to inhibit SRB related corrosion. Vessels which are used to store liquids designed for human consumption, such as milk and beer, and which are regularly sterilized by, for example, contact with live steam, will not, however, typically be protected against corrosion using the invention.

Aviation and other fuel tanks also constitute closed systems. As noted earlier, corrosion in these systems can be caused by bacterial (pseudomonad) or fungal contamination. In this setting, a bacteria such as *Serratia*, modified to secrete an anti-fungal or an antimicrobial agent which inhibits the target organism (such as a pseudomonad), can be introduced to reduce corrosion from these sources. For continued protection of the system, it is generally desirable that the antimicrobial agent chosen for secretion be less toxic to the organism which will secrete it than it is to the fungus, pseudomonad, or other target organism.

2. Open Systems

Systems which routinely or regularly discharge their contents into the environment (with or without intervening treatment) may be considered open systems. Such systems include municipal sewage systems, storm sewers, and drainage systems, which typically comprise concrete conduits which are subjected to relatively prolonged or repeated immersion in or exposure to water or other liquids. Such conduits are subject to SRB related corrosion due to the formation of sulfuric acid by sulfur-oxidizing bacteria from the hydrogen sulfide generated by SRB. Accordingly, inhibition of SRB in these and similar concrete conduits by means of the invention can reduce the corrosion of these structures.

3. Structures Exposed to the Environment

A great number of metal and concrete structures, such as bridges, railway trestles, highway overpasses, and the like, are exposed to the environment in frequent or constant contact with water, permitting the development of biofilms on the surface. SRB related corrosion of these structures can be inhibited by use of the invention.

EXAMPLES

The invention is illustrated by the following examples. These examples are offered to illustrate, but not to limit, the present invention.

Example 1

Biofilm Architecture and Correlation to Corrosion Inhibition

The main objectives of this study were to characterize the protective biofilm architecture and correlate the biofilm constituents to corrosion inhibition. Biofilms were stained for live cells, dead cells, and exopolysaccharide, visualized using confocal scanning laser microscopy ("CSLM"), and quantified to obtain depth profiles. The effect of increasing temperature and growth medium salt content both on the biofilm composition and corrosion inhibition was studied.

Materials and Methods

Bacterial Strains, Growth Media, and Culture Conditions.

A kanamycin-resistant, transposon mutant of the spoiled-meat bacterium *P. fragi* ATCC 4973 ("*P. fragi* K"), (Jayaraman, A. et al. 1997a) and a tetracycline-resistant enteric bacterium, *E. coli* DH5α(pKMY319) (Jayaraman, A. et al. 1997a), were used based on their ability to form biofilms (Parolis, L. A. S. et al. *Carbohydrate Research* 216:495–504 (1991); Huang, C.-T. et al. *Biotechnology and Bioengineer-*

*ing* 41:211–220 (1993)). Both strains were cultivated without shaking at 23° C. or 30° C. in 250 ml Erlenmeyer flasks with multiple SAE 1018 metal coupons in 35 ml of Luria-Bertani medium (hereafter, "LB;") (Maniatis, T. et al., Molecular cloning: A laboratory manual, Cold Spring Harbor Laboratory Press, Cold Spring Harbor, N.Y. (1982)) (hereafter, Maniatis et al., 1982) and Vaatanen nine salts solution ("VNSS," Hernandez, G. et al. *Corrosion* 50:603–608 (1994)) (hereafter, Hernandez et al., 1994) supplemented with 50 µg ml$^{-1}$ of kanamycin (Jayaraman, A. et al. 1997a) or 25 µg ml$^{-1}$ of tetracycline (Yen, K.-M. *Journal of Bacteriology* 173:5328–5335 (1991)). All strains were streaked from a −85° C. glycerol stock onto LB agar plates with appropriate antibiotics. A single colony was then picked and used to inoculate 10 ml of growth medium with suitable antibiotics and grown overnight at 30° C., 250 rpm (Series 25 shaker, New Brunswick Scientific, Edison, N.J.). A 0.1% inoculum (350 µl) was used for developing biofilms for the corrosion experiments. Medium replenishment was by slow removal of the old medium and gentle addition of fresh medium along the walls of the Erlenmeyer flask.

Metal Coupon Preparation and Mass Loss Determination.

SAE 1018 steel coupons weighing 5.1 grams and having a diameter of 25.5 mm and a thickness of 1.2 mm were cut from sheet stock and polished with 240 grit polishing paper (Buehler, Lake Bluff, Ill.) and prepared as reported previously (Jayaraman et al. 1997a). The specific mass loss observed (mg sq. cm$^{-1}$) was determined by dividing by the total surface area of the coupon (11.18 sq. cm) and was used as an indicator of the extent of corrosion (Jayaraman et al. 1997a). All corrosion experiments were performed with three replicates.

Confocal Scanning Laser Microscopy (CSLM) and Determination of Biofilm Thickness.

Metal coupons with attached surface biofilms were removed from Erlenmeyer flasks and immersed once in 0.85% NaCl to remove bulk supernatant cells. Cells and polysaccharide were stained for 30 min simultaneously in 4 ml of staining solution using the Live/Dead Baclit bacteria viability assay kit protocol (1.125 µl ml$^{-1}$ of each stain component, Molecular Probes (Eugene, Oreg.)) and calcofluor (300 µl ml$^{-1}$, Sigma (St. Louis, Mo.), Stewart et al. 1995). The live/dead viability kit distinguishes live and dead cells based on membrane integrity; live cells with intact membranes stain green, and dead cells with compromised membranes stain red. The stained coupons were transported to the stage of a confocal scanning laser microscope (MRC 600, Bio-Rad, Hercules, Calif.) equipped with a krypton/argon laser, and a 60×, 1.4 NA oil-immersion lens. To minimize the damage to the biofilm when placed on the stage of the inverted microscope, a 1.8 cm diameter coverslip (circles No. 1, 1.3 to 1.7 cm thick, Fisher Scientific Co., Pittsburgh, Pa.) was gently placed on the coupon (held by capillary action), and the coupon (2.55 cm diameter) was held by the circular microscope aperture (2.0 cm diameter) in the area outside of the coverslip. The central area of the biofilm was not compressed by the weight of the coupon and only this area was visualized.

The sample was excited at 488 nm, and the fluorescent light was imaged using the K1/K2 filter block combination. The biofilms were analyzed using a MRC 1024 confocal microscope (Bio-Rad, Hercules, Calif.) with a T1/E2 multipurpose filter combination. Thin optical sections (horizontal sectioning) of 0.5 to 1.0 µm were collected over the complete biofilm thickness for a representative position (chosen as one of four similar positions in the biofilm on the same coupon). The biofilm thickness was found by focusing on the top and bottom of a biofilm with the distance traveled corrected for refractive index (Bakke, R. and Olsson, P. Q., *Journal of Microbiological Methods* 6:93–98 (1986)) and the thickness was determined as the average of the four similar positions analyzed on the same coupon.

Image Analysis.

Image processing and analysis of all biofilms were performed with the COMOS software available on the Bio-Rad MRC600. Optical sections were discriminated based on pixel intensities to differentiate live and dead cells, polysaccharide, and void space. The percentage of each section area covered by a range of pixel intensities was then measured to obtain the relative proportions of the component in each section; these relative proportions of each component were plotted as a function of the normalized depth (depth at which the image was obtained divided by the total biofilm thickness). Accordingly, position 0.0 represents the biofilm-liquid interface and position 1.0 represents the biofilm-metal interface.

RESULTS

Corrosion Inhibition with *P. fragi* and *E. coli*.

Mass loss in LB medium and VNSS medium with *P. fragi* K or *E. coli* DH5α(pKMY319) was examined for 8 days in stationary batch cultures at 23° C. and 30° C. in which the growth medium was either replenished daily or left unchanged for eight days. The metal coupons immersed in bacterial suspensions showed a 2.3 to 6.9-fold decrease in mass loss after eight days compared to coupons immersed in sterile media. These results compare well to those of Jayaraman et al. (1997a) and Pedersen and Hermansson, 1989) who reported an eight-fold reduction in corrosion of SIS 1146 steel using *Pseudomonas* S9 and *Serratia marscens* after 19 days of exposure in VNSS medium. Previous work in our laboratory has shown that there is no difference in the corrosion of SAE 1018 steel coupons in sterile, fresh LB medium and spent, filtered LB medium (Jayaraman et al., 1997a).

The eight-day mass loss observed with *P. fragi* K and *E. coli* DH5α varied with the growth medium and the cultivation temperature. The total mass lost was less at the lower temperature for both media; however, corrosion inhibition (as a percentage reduction in mass loss of the sterile control) was comparable or higher at the higher temperature in both media. The mass loss with both strains at both temperatures was less in LB medium compared to VNSS medium. Daily replenishment of the medium did not significantly affect corrosion inhibition except with *P. fragi* K in VNSS medium at 30° C. where corrosion inhibition was nearly 2.3-fold better. Irrespective of medium replenishment, *E. coli* DH5α (pKMY319) resulted in a higher mass loss than *P. fragi* K at 23° C., and the mass loss in the presence of both strains was comparable at 30° C. Sterile controls corroded to the same extent irrespective of whether the medium was replaced daily.

Metal coupons in most suspensions of bacteria corroded at a rate of approximately 0.03–0.06 mg sq. cm$^{-1}$ day$^{-1}$ during the first four days. The corrosion rate decreased beyond four days. Sterile controls corroded at a slightly faster rate in VNSS medium than in LB medium at both temperatures, and the corrosion rate was relatively uniform for the entire eight-day period.

Determination of Biofilm Thickness by CSLM.

Multiple coupons were removed from the medium after 2, 3, 4 and 8 days, stained for cells and polysaccharide simultaneously, and analyzed by CSLM. Biofilms observed under 100× magnification (no coverslip) and 600× magnification (with coverslip) showed a similar depth profile of live and dead cells and polysaccharide.

Both *P. fragi* K and *E. coli* DH5α(pKMY319) biofilms developed to a detectable thickness (~10–15 μm) within the first 48 hours of exposure to growth media (data not shown). *P. fragi* K biofilms did not vary significantly in thickness for different growth temperatures, media, and medium replenishment, and the biofilm was approximately 14 μm thick after four days; the biofilm thickness was approximately 12 μm after eight days of exposure. *E. coli* DH5α(pKMY319) exhibited a similar trend, with a four-day biofilm (13 μm) being slightly thicker than an eight-day biofilm (~11 μm).

Characterization of the Biofilms.

*P. fragi* K and *E. coli* DH5α(pKMY319) biofilms in LB and VNSS medium with and without medium replenishment at 23 and 30° C. were characterized and analyzed using image analysis to create four-day normalized depth profiles.

As a control experiment to verify that the Live/Dead stain can be used to quantify populations with live and dead cells, 200 μg ml$^{-1}$ of kanamycin was added to a 12-hour wild-type *P. fragi* culture and visualized with CSLM after 48 hours. The sample was predominantly red (approximately 75%), with a few green and yellow cells. The biofilm sample was also streaked on LB agar plates and minimal growth was observed along the main streak path (whereas cells not exposed to antibiotic grew as a bacterial lawn along the main streak). Hence, the stain can be used for identifying and quantifying dead cells.

Horizontal sections at each 1.0 μm of depth of *P. fragi* K and *E. coli* DH5α(pKMY319) biofilms were obtained with the confocal microscope, and the distribution of live cells, dead cells, exopolysaccharide (EPS) and void spaces were determined. Both *P. fragi* K and *E. coli* DH5α(pKMY319) biofilms consisted of uniform layers of cells and polysaccharide (whenever present) near the metal surface. The ratio of cellular (live and dead cells) to non-cellular matter (polysaccharide and water channels) varied with depth for all biofilms. Biofilms of both strains exhibited a pyramidal architecture, with a dense concentration of cells near the bottom of the biofilm (biofilm-metal interface) and a sparse distribution of cells near the biofilm-liquid interface. This is in agreement with Lawrence et al., *J. Bacteriol.* 173:6558–6567 (1991), who reported a similar pyramidal structure for *P. fluorescens* and *P. aeruginosa* biofilms developed on glass slides in complex and minimal media with continuous cultures. In the work reported here, the top layers of the biofilm predominantly consisted of live cells, and the live-cell density decreased near the metal surface. Polysaccharide (when present) was usually detected near the bottom of the biofilm (typically at 3 μm from the metal surface). Thick clumps of loosely-associated live and dead cells (15 to 40 μm thick) were present at the top of the biofilm (at the biofilm-liquid interface) and were not considered for determination of biofilm thickness. *E coli* DH5α (pKMY319) biofilms also had a thin layer of slime covering the metal coupons after 8 days of exposure to growth medium which could not be retained on top of the metal coupon during the staining procedure.

The *P. fragi* K four-day depth profiles in LB and VNSS medium at 30° C. were determined. More cells were detected in *P. fragi* K and *E. coli* DH5α biofilms grown in LB medium than in VNSS medium at 30° C. Furthermore, more cell mass was formed with *P. fragi* at higher temperatures in LB medium since at 23° C., 50% of the biofilm was made up of live and dead cells, whereas biofilms grown at 30° C. had 90% live and dead cells. In biofilms developed in VNSS medium, polysaccharide accounted for nearly 10 to 55% of the biofilm whereas in LB medium less than 5% EPS was detected.

By replacing the medium daily, the relative proportions of the biofilm constituents changed significantly; typically, more live cells were detected in the biofilm under all conditions. The biofilm architecture also changed with the addition of fresh medium daily with nearly equal proportions of cells observed at all depths of the biofilm instead of a pyramidal architecture. The ratio of cellular material to non-cellular material remained relatively constant throughout the biofilm for most conditions, and polysaccharide was observed only in VNSS medium. The extent of polysaccharide production (whenever present) was greater with medium replenishment. Less clumping was observed at the upper layers of the biofilm, and the proportion of live cells also did not decrease significantly towards the bottom of the biofilm.

CONCLUSION

CSLM image analysis of the biofilms and quantification of the relative proportions of live cells, dead cells, EPS, and void space revealed that the maximum cell (live and dead) density was obtained after four days of exposure and decreased beyond four days. Therefore, four-day batch culture biofilms of *P. fragi* K and *E. coli* DH5α(pKMY319) grown on metal coupons in LB medium and VNSS medium were selected for further characterization and comparison with four-day biofilms grown with daily medium replenishment.

The composition of the biofilms depended on the growth medium, temperature of cultivation, and medium replenishment. Development of biofilms in LB medium beyond four days showed a decrease in cell number suggesting that the absence of a polysaccharide matrix causes detachment of cells. In VNSS medium, the cells were embedded in a polysaccharide matrix and showed a lesser tendency to detach from the metal surface on exposure beyond eight days (not shown). This compares well with Dewanti and Wong, *Int'l. J. Food Microbiol.*, 26:147–164 (1995), who observed a similar biofilm structure with *E. coli* O157:H7 grown in trypticase soy broth and minimal media. Further, the physiology and cell morphology of the biofilm bacteria was different in biofilms developed in different media and temperatures. *P. fragi* and *E. coli* biofilms developed in LB medium were observed as small and distinct cells; in contrast, biofilms in VNSS medium were elongated and in clusters, probably as a response to environmental stress.

Replenishing the growth medium daily caused a small decrease in the cellular content throughout the depth of the biofilm and less clumping was observed. The continuous availability of nutrients could possibly enhance the attachment of metabolically active cells to the biofilm, causing addition of cells at the top of the biofilm to replace lost cells and is consistent with the observations of Costerton (1995). The absence of clumping at the biofilm-liquid interface could also be explained by the minimal disturbance to the biofilm architecture caused by the daily addition of fresh growth medium and the staining procedure.

The characteristics of the biofilms (discerned through CSLM), when compared to the corrosion results, indicate that increasing the total cells in the biofilm increases corrosion inhibition. Increasing the temperature from 23° C. to 30° C. resulted in a 100% increase in corrosion for the sterile controls and a 1.6 to 4.1-fold increase in cell mass (calculated as the average total live and dead cells along the entire depth profile of the biofilm) for six of the eight conditions studied (two bacteria, two media, and two temperatures). Corresponding to this increase in cell mass and temperature, there was only a 22% increase in corrosion for six of eight biofilm conditions (for *E. coli* DH5α in VNSS medium with daily replenishment, corrosion increased 100%; and for *P. fragi* K in VNSS medium without replenishment, corrosion increased 230%). Hence, in general, increasing temperature increased cell mass, and the increase in corrosion for coupons protected by biofilms were much less than that seen with sterile media (22% vs. 100%).

Previous work in our laboratory on corrosion inhibition with seven widely varying bacterial genera (with differing degrees of biofilm formation) confirm that a homogenous biofilm is necessary (Jayaraman et al. 1997b): metal coupons exposed to bacterial suspensions of *Streptomyces* (which formed a sparse biofilm with cells distributed in clumps) corroded at a rate comparable to sterile controls. Since the ratio of corrosion in this study after four days with *P. fragi* to corrosion in a similar sterile control is comparable at 23° C. and 30° C. with LB medium and VNSS medium, however, similar corrosion inhibition is afforded by the biofilm even though the thickness, composition, and characteristics of the biofilm under the four conditions are drastically different. Hence, it appears that a certain minimum biofilm thickness or density is required for corrosion inhibition. Similar results occurred with *E. coli* in VNSS medium at 30° C.

When the growth medium was replenished daily, it was interesting to note that significant differences in corrosion inhibition were seen only in VNSS medium at 30° C. Apart from increasing or decreasing the thickness of the biofilm, one of the main differences seen by replenishing the medium was the increase in the uniformity of the distribution of cells throughout the biofilm and an increase in the relative proportion of live cells. This uniform layer of cells could reduce the amount of oxygen available at the metal surface for the corrosion process, and thereby inhibit corrosion. The lack of a significant change in corrosion inhibition compared to not replenishing the medium for other conditions also suggests an upper limit for corrosion inhibition by a particular bacterium which is quickly reached in a uniform biofilm by a minimum number of actively respiring cells.

Example 2

Biofilms can Inhibit Corrosion of Copper and Aluminum

This example shows that biofilms can inhibit corrosion of copper and aluminum.

The toxicity of copper to microorganisms has led to the belief that microbial induced corrosion (MIC) of copper is insignificant (Iverson, 1987). However, ammonia generated by the microorganisms and sulfuric acid generated by *Thiobacillus* and sulfate-reducing bacteria (SRB) can cause corrosion of copper alloys (Iverson, 1987); Wagner and Little, 1993). Wagner and Little observe that the presence of a biofilm on copper creates differential aeration cells and chloride gradients which can cause pitting (Wagner and Little, 1993). Corrosion of copper alloys is a problem in heat exchanger tubing, ship seawater piping, and aircraft fuel tanks (Iverson, 1987; Miller, 1981). Iverson also mentions that the corrosion of copper in fresh water and seawater was inhibited by the addition of bacteria and corrosion increased after the bacteria died (Iverson, 1987).

Formation of an oxide passive film by aluminum enhances its corrosion resistance (Iverson, 1987; Wagner and Little, 1993). *Pseudomonas* and *Cladosporium* have been commonly associated with the MIC of aluminum and its alloys (Iverson, 1987). The production of corrosive organic compounds by *P. aeruginosa* can remove zinc and magnesium from aluminum and alloys and cause corrosion. The pitting of aluminum by three strains of SRB has been reported and a 100-fold increase in weight loss compared to sterile controls was observed (Iverson, 1987).

Materials and Methods

Bacterial Strains and Growth Medium.

*P. fragi* K is a kanamycin-resistant derivative of *P. fragi* (Jayaraman, A. et al. 1997a), and *B. brevis* 18 is a gramicidin S-overproducing strain (Azuma, T. et al. *Appl. Microbiol. Biotechnol.* 38:173–178 (1992)) (hereafter, Azuma et al., 1992). Biofilms on metal surfaces were developed in continuous reactors with modified Baar's medium as described earlier by Jayaraman et al. (Jayaraman, A. et al., 1997c) since this medium supports the growth of aerobes and SRB.

Sample Preparation.

Unalloyed copper and aluminum alloy 2024 plates (7.5 cm×7.5 cm squares and 1.2 cm thick) were cut from sheet stock, polished with 240 grit paper (Buehler, Lake Bluff, Ill.), and stored as described earlier (Jayaraman, A. et al. 1997c).

Continuous Corrosion Rates Using EIS.

Impedance data (from a minimum of two experiments) was obtained using a Solarton-Schlumberger electrochemical measurement unit (SI 1280, Schlumberger Technical Instruments Division, San Jose, Calif.) interfaced to a Macintosh computer (PowerMac 7100/80, Apple Computers, Cupertino, Calif.) running EISIS electrochemical experimentation software (University of California, Irvine) (equivalent software, THALES Impedance Measurement and Equivalent Circuit Synthesis/Simulation/Fitting Software, is available commercially from Bioanalytical Systems, Inc., West Lafayette, Ind.) (hereafter, THALES software). The reactor configuration and operating conditions were as described earlier (Borenstein, 1994, supra).

RESULTS AND DISCUSSION

The polarization resistance $R_p$, capacitance C, and corrosion potential $E_{corr}$ of all experiments with copper and aluminum are summarized in Table I. Corrosion with unalloyed copper in modified Baar's medium at 30° C. was studied using continuous reactors and the impedance spectra obtained. Sterile reactors (five independent experiments) had a maximum phase angle of approximately 56° after 10 days of exposure. A *P. fragi* K biofilm grown on copper (five independent experiments) increased the impedance by 21-fold at the lowest frequency measured ($1.4 \times 10^{-3}$ Hz) in the same time period, indicating a decrease in corrosion. This decrease in corrosion was also corroborated by an increase in the phase angle (c.f., 56° vs. 71°). Similar impedance spectra (two independent experiments) were also observed when a *B. brevis* 18 biofilm was developed on copper.

The impedance spectra obtained with sterile modified Baar's medium with aluminum alloy 2024 in continuous reactors (two independent experiments) showed a maximum phase angle of 71° at the low frequencies after 10 days of exposure. When a *P. fragi* K biofilm was developed on the aluminum alloy for six days (five independent experiments), the maximum phase angle shifted to 78°, and an 8-fold increase in $R_p$ was also observed. As seen with unalloyed copper, a *B. brevis* 18 biofilm (three independent experiments) was also capable of increasing $R_p$ of aluminum 2024 by 5-fold and the phase angle by 7° under similar conditions.

The observed increases in $R_p$ and the changes in the impedance spectra are similar to the observations of Jayaraman et al. 1997c, who reported a 40-fold decrease in $R_p$ and a 35° increase in the phase angle of SAE 1018 mild steel with an axenic *P. fragi* K biofilm compared to sterile controls.

TABLE I

Polarization resistance $R_p$, capacitance C, and corrosion potential $E_{corr}$ of unalloyed copper and aluminum 2024 alloy in modified Baar's medium at 30° C. Data are from a representative experiment (minimum of two independent experiments).

| Experiment | $R_p$ (Ohm * cm$^2$) | C (F/cm$^2$) | $E_{corr}$ (mV vs. Ag/AgCl) | Sample |
|---|---|---|---|---|
| Sterile | note 1 | note 1 | −171 | Copper |
| *P. fragi* K | note 2 | note 2 | −118 | Copper |
| *B. brevis* 18 | 9.66 × 10$^5$ | 1.65 × 10$^{-3}$ | −177 | Copper |
| Sterile | 3.04 × 10$^4$ | 1.78 × 10$^{-5}$ | −670 | Aluminum 2024 |
| *P. fragi* K | 1.32 × 10$^5$ | 4.05 × 10$^{-5}$ | −520 | Aluminum 2024 |
| *B. brevis* 18 | 2.13 × 10$^5$ | 1.69 × 10$^{-5}$ | −512 | Aluminum 2024 | note 1: Not possible to estimate parameters based on available equivalent circuit models
note 2: Impedance suggests pitting (C = 8.1 × 10$^{-5}$ F/cm$^2$, Rp = 2.97 × 10$^5$ Ohm * cm$^2$, $R_{pit}$/F = 3.52 × 10$^3$ Ohm)

Example 3

Peptide Antimicrobial Agents Inhibit the Growth of SRB

This example demonstrates that peptide antimicrobial agents inhibit the growth of SRB.

Peptide antimicrobials are small (Marahiel M. et al. *Mol. Microbiol.* 7:631–636 (1993); Nakano M. M. and Zuber, P., *Crit. Rev. Biotechnol.* 10:223–240 (1990)), may be cloned readily in biofilm-forming aerobic bacteria, and may be optimized through protein engineering (Piers K. K. et al. *Gene* 134:7–13 (1993)) (hereafter, Piers, 1993); hence, they are attractive candidates for excluding SRB from biofilms.

Saleh et al. (1964) and Postgate (Postgate J. R. *The sulphate-reducing bacteria*. Cambridge University Press, New York (1984)) (hereafter, Postgate, 1984) have compiled lists of antimicrobials which are inhibitory to various SRB, which include the peptide polymyxin B (which inhibits *D. vulgaris* at 100 μg/mL). The present study describes inhibition of the representative SRB *D. vulgaris* and *D. gigas* in suspension cultures by the peptide antimicrobials gramicidin S (a 10 amino acid cyclic peptide from *B. brevis* (Azuma et al., 1992), gramicidin D (a 15 amino acid linear peptide from *B. brevis* (van Döhren H., Peptides. In L. C. Vining and C. Stuttard (ed.), *Genetics and Biochemistry of Antibiotic Production*. Butterworth-Heinemann, Boston (1995)), amidated and non-amidated indolicidin (a 13 amino acid linear peptide from bovine neutrophils (Falla T. J. et al. *J. Biol. Chem.* 271:19298–19303 (1996) (hereafter, Falla et al., 1996); Selsted M. E. et al., *J. Biol. Chem.* 267:4292–4295 (1992)) (hereafter, Selsted et al., 1992), bactenecin (a 12 amino acid cyclic peptide from bovine neutrophils (Romeo D. et al. *J. Biol. Chem.* 263:9573–9575 (1988)) (hereafter, Romeo et al., 1988), and polymyxin B (a 10 amino acid branched cyclic decapeptide from *Bacillus polymyxa* (Fujita-Ichikawa Y. and K. Tochikubo, *Microbiol. Immunol.* 37:935–941 (1993)).

Materials and Methods
Bacterial Strains and Growth Medium.
*D. vulgaris* (ATCC 29579) and *D. gigas* (ATCC 19364) were obtained from the American Type Culture Collection and cultivated in 15 mL screwcap tubes with 10 mL of modified Baar's medium (ATCC medium 1249) supplemented with 100 μL each of the oxygen-scavengers 4% sodium sulfide and Oxyrase (Oxyrase Inc., Mansfeld, Ohio). Initial cultures were grown from −85° C. glycerol stocks; all subsequent cultures were grown with a 3% inoculum from the initial culture maintained at 30° C. without shaking. Both SRB were routinely cultured in tightly closed screwcap tubes and exposed to oxygen in laminar flow hoods (which did not inhibit cultivation as has been earlier reported by Angell, P. and White, D. C., *J. Ind. Microb.* 15:329–332 (1995)). SRB were also cultured periodically in the presence of 0.1% ferrous ammonium sulfate, and the presence of these sulfate-reducers was confirmed by the detection of black iron sulfide in the culture tubes. The desulfoviridin assay was also performed after each MPN assay to confirm the presence of *D. vulgaris* or *D. gigas* by its red color under UV light due to the release of the chromophore of the pigment desulfoviridin. (Postgate, 1984).

Antimicrobial Peptides.
Indolicidin (amidated and free-acid form) was kindly provided by Prof. Michael E. Selsted of UC Irvine, and the free-acid form was synthesized by Genosys Biotechnologies Inc. (The Woodlands, Tex.) at 76% purity. Gramicidin S (96.5% purity) & Gramicidin D (100% purity), and polymyxin B (100% purity) were purchased from Sigma Chemical Co. (St. Louis, Mo.). Bactenecin was synthesized by Genosys Biotechnologies Inc. at 32% purity, and shipped in the presence of dithiothreitol ("DTT") (<0.1%). The molecular weights of the synthesized indolicidin (acid form, 1907 Da) and bactenecin (1486 Da) were verified using a MALDI-Time of Flight (TOF) mass spectrometer (Voyager DE 5-2386-00, Perseptive Biosystems, Mass.).

A Vydac C18 column (Vydac, Hesperia, Calif.) was used on a reverse-phase HPLC (Varian Vista 5000 series, Sugar Land, Tex.) to remove the residual DTT from bactenecin (and to facilitate the formation of a disulfide bond between residues 3 and 11). A mobile phase of acetonitrile/0.1% trifluoroacetic acid (TFA) in water (20:80) was used to elute the DTT followed by a step-change to a 50:50 acetonitrile/0.1% TFA in water system to elute bactenecin. This fraction was considered free of DTT and used for antimicrobial assays.

SRB Inhibitory Assays.
For determining the viability indices (Romeo, et al., 1988) of SRB, a late-exponential phase culture (O.D$_{600}$ 0.16 to 0.19 which corresponded to an initial cell number of 5–9× 10$^4$ cells/mL) was exposed to various concentrations of antimicrobials for 1 hour at 30° C. One mL of cells was harvested, washed once in fresh modified Baar's medium to remove cellular debris, and resuspended in 1 mL of fresh modified Baar's medium supplemented with 10 μL each of Oxyrase (Oxyrase Inc., Mansfeld, Ohio) and 4% sodium sulphide. Aliquots of 450 μL were dispensed in 500 μL sterile eppendorf tubes and appropriate amounts of antimicrobials added and incubated at 30° C. The effectiveness of treatment was determined by the multiple-tube most-probable-number (MPN) fermentation technique. (Anonymous. Multiple-tube fermentation technique for members of the coliform group, pp. 9–45 to 9–51. In A. E. Greenberg, L. S. Clesceri, and A. D. Eaton (eds.), *Standard Methods for the Examination of Water and Wastewater*, 18 ed. American Public Health Association, American Water Works Association, and Water Pollution Control Federation, New York (1992)) (hereafter, Greenberg, 1992).

The MPN test for enumerating SRB was performed in three 12 mL tubes with a 1000 µL inoculum of SRB, three 12 mL tubes with a 500 µL inoculum, and three 12 mL tubes with a 100 µL inoculum. All nine tubes contained a final volume of 10 mL of modified Baar's medium supplemented with 100 µL each of 4% sodium sulfide and Oxyrase (Oxyrase Inc., Mansfeld, Ohio). The tubes were monitored for 72 hours to determine the number of tubes that were positive for growth. Growth was determined by the increase in culture turbidity, and the MPN index/mL was calculated using the Thomas formula. (Greenberg 1992).

RESULTS AND DISCUSSION

*D. vulgaris* and *D. gigas* were incubated in the presence of various antimicrobial peptides, and their viability after one-hour exposure was determined. Ampicillin was used as a positive control for *D. vulgaris*, as it and chloramphenicol were found to inhibit this strain at 20 µg/mL, which agreed with previous reports (Odom and Singleton, *The sulfate-reducing bacteria: contemporary perspectives*, Springer Verlag, New York (1993) (hereafter, Odom and Singleton, 1993); however, neither ampicillin nor chloramphenicol were effective in inhibiting *D. gigas* at 100 µg/mL. The susceptibilty of both SRB to several additional antibiotics (kanamycin, tetracycline, thiostrepton, penicillin G, and naladixic acid), inorganics (ammonium molybdate, sodium molybdate, and anthraquinone), and peptides (nisin and polymyxin B) was also evaluated using stationary-phase cultures of SRB. *D. gigas* was inhibited by anthraquinone at 100 µg/mL (Cooling et al., 1996), and both SRB were inhibited by sodium molybdate at 100 µg/mL. This is similar to the observation of Saleh, et al., 1964, who surveyed nearly 200 compounds for their SRB-inhibitory activity and noted that SRB show a high degree of resistance to inhibitory compounds (Id.).

The MPN assay was used to determine the viability index of *D. gigas* and *D. vulgaris* for the peptide antimicrobials. For *D. gigas*, both gramicidin S and the amidated form of indolicidin, Ind-NH$_2$ (which is the naturally occurring form in bovine neutrophils (Falla et al., 1996); Selsted et al., 1992), were capable of reducing the viability of a late-exponential-phase culture by 92–96% after a one-hour exposure at 25 µg/mL. For *D. vulgaris*, Ind-NH$_2$ at 25 µg/mL was slightly more effective in inhibiting growth (viability reduced by 99.3%), while gramicidin S was less effective and reduced viability by 93% at 100 µg/mL. The acid form of indolicidin (Ind-OH) was 10-fold less effective than the amidated form of indolcidin against *D. gigas* and 174-fold less effective against *D. vulgaris* at 25 µg/mL. This is not surprising as the post-translational amidation is thought to increase the potency of indolicidin (Falla, et al., 1996). The peptide antimicrobials gramicidin D, polymyxin B, and bactenecin (Postgate, 1984) were also capable of decreasing the viability of *D. vulgaris* and *D. gigas* by approximately 90% at 100 µg/mL. These MPN assay results were also corroborated by the similar results obtained when *D. vulgaris* was exposed to gramicidin S, gramicidin D, indolicidin, and bactenecin for one hour, plated on *Desulfovibrio* agar (ATCC medium 42), and incubated in anaerobic GasPak chambers (Fisher Scientific Co., Pittsburgh, Pa.).

These results indicate that peptide antimicrobials like gramicidin S, indolicidin, polymyxin B, and bactenecin have potential to be used to inhibit the growth of SRB and decrease microbially influenced corrosion of steel. Indolicidin is capable of inhibiting *Escherichia coli* and *Staphylococcus aureus* by 99.9% at 5–25 µg/mL (Romeo et al., 1988; Selsted et al., 1992); but, in this study, *D. gigas* and *D. vulgaris* exhibited greater resistance to indolicidin. Bactenecin inhibits *E coli* by 95% at 100 µg/mL (Romeo et al., 1988) and demonstrated comparable inhibition of *D. gigas* and *D. vulgaris* (90%) in this study. Gramicidin S has also been known to completely inhibit growth of Gram-negative bacteria at 3–12.5 µg/mL (Kondejewski L. et al., *Int. J. Peptide Protein Res.* 47:460–466 (1996)) and demonstrated an inhibitory effect against both Gram-negative SRB in this study at 50–100 µg/mL. Based on their activity against SRB in suspension cultures, all the antimicrobial peptides tested in this study were more potent at comparable concentrations than commercially available antibiotics like kanamycin, naladixic acid, and tetracycline and inorganics like sodium molybdate and anthraquinone.

Example 4

Exclusion of SRB from Biofilms Using Bacteria Secreting Cloned Antimicrobial Agents This example shows the cloning and expression of antimicrobial chemical agents in bacteria and their use to exclude SRB from a biofilm on stainless steel.

Antimicrobial peptides have been identified and isolated from several bacteria (Hancock, R. E. W. et al., *Adv. Microb. Physiol.* 37:135–175 (1995), plants (Hancock, R. W. et al., Cationic peptides: a class of antibiotics able to access the self-promoted uptake pathway across the *Pseudomonas aeruginosa* outer membrane, p. 441–450, In T. Nakazawa (ed.), *Molecular Biology of the Pseudomonads*, ASM press, Washington D.C. (1996)) (hereafter, Hancock et al., 1996), insects (Boman, H. G. et al., *Eur. J. Biochem.* 20:23–31 (1991)), and mammals (Frank, R. W. et al., *J. Biol. Chem.* 265(31):18871–18874 (1990); Lehrer, R. I. et al., *Annu. Rev. Immunol.* 11:105–128 (1993); Zasloff, M. *Proc. Natl. Acad. Sci.* 84:5449–5453 (1987)) (hereafter, Zasloff, 1987). These peptides can be broadly classified into magainins (Zasloff, 1987), defensins (Cullor, J. S. et al., *Arch. Opthalmol.* 108:861–864 (1990)) (hereafter, Cullor et al., 1990), cecropins (Calloway, J. W. et al., *Antimicrob. Agents Chemother.* 37:1614–1619 (1993)) (hereafter Calloway et at., 1993); melittins (Piers, K. L. et al., *Mol. Microbiol.* 12(6):951–958 (1994)) (hereafter, Piers et al., 1994) and have been shown to demonstrate antimicrobial activity against Gram-negative and Gram-positive bacteria as well as yeast and fungus (Hancock et al., 1996). Most cationic peptides have multiple lysine and arginine residues and hydrophilic and hydrophobic faces (Hancock et al., 1996) and kill microorganisms by increasing the permeability of the bacterial cell membrane or by inhibiting DNA synthesis (Hancock et al., 1996; Romeo et al., 1988).

Indolicidin (Cullor et al., 1990; Del Sal, G. et al., *Biochem. Biophys. Res. Comm.* 187(1):467–472 (1992)) and bactenecin (Frank, R. W. et al., *J. Biol. Chem.* 265(31): 18871–18874 (1990); Romeo et al. 1988)) are cationic antimicrobial peptides isolated from bovine neutrophils (Lehrer, R. I. et al., *Annu. Rev. Immunol.* 11: 105–128 (1993)). Indolicidin is a tridecapeptide which belongs to the family of defensins (Selsted et al., 1992) and consists only of six different amino acids with the highest proportion of tryptophan (39%) in any known protein (Falla et al., 1996). Indolicidin is also the smallest known linear antimicrobial peptide, and its carboxyl terminus is amidated in its naturally occurring form (Falla et al., 1996; Selsted et al., 1992).

Bactenecin is an arginine-rich, cyclic dodecapeptide and contains a disulfide bond which maintains the cyclic structure (Romeo et al., 1988).

Few attempts have been made at producing antimicrobial peptides in prokarytoic and eukaryotic expression systems for commercial applications. Piers et al. (Piers et al., 1993 and Piers et al., 1994) have described procedures for synthesizing and purifying the human neutrophil peptide 1 (HNP-1) and a cecropin/melittin hybrid peptide in bacteria using a *Staphylococcus aureus* expression system. These peptides were synthesized as fusions to Protein A, secreted into the culture medium, and purified using affinity chromatography (Piers et al., 1993). Calloway (Calloway et al., 1993) tried to express cecropin A in *E. coli* and concluded that post-translational modification of the carboxyl terminus was required for high antimicrobial activity. Hara and Yamakawa (Hara, S. and M. Yamakawa, *Biochem. Biophys. Res. Comm.* 224(3):877–878 (1996)) have produced the peptide moricin in *E. coli* as a fusion to the maltose-binding protein and found activity comparable to the native protein. Haught et al. (*Biotechnol. Bioeng.* 57:55–61 (1998)) have reported the production of the recombinant antisense antimicrobial peptide P2 in *E. coli* as inclusion bodies using a fusion to bovine prochymosin; high levels of the protein were expressed (nearly 16% of total cell protein). Pang et al. (*Gene*, 116:165–172 (1992)) (hereafter, Pang et al., 1992) have tried to express and secrete the scorpion insectotoxin $I_5A$ in bacteria, yeast, and tobacco plants (no measurable activity was detected). All these approaches were targeted to large-scale, inexpensive production of purified antimicrobial peptides rather than in vivo applications.

In the previous example, we showed that the purified antimicrobial peptides indolicidin, non-amidated indolicidin, and bactenecin inhibit anaerobic SRB in suspension cultures. This example shows that production of antimicrobial peptides in aerobic biofilm-forming bacteria can exclude SRB from the biofilms and inhibit SRB-induced corrosion of metal. In particular, this example demonstrates the expression of the cationic antimicrobial peptides indolicidin and bactenecin in Gram-positive *Bacillus* and their use in excluding SRB in biofilms on 304 stainless steel. Indolicidin and bactenecin have been cloned as fusions to the alkaline protease (apr) signal sequence and expressed constitutively using the apr promoter. The pro-region of barnase (an extracellular RNase from *B. amyloliquefaciens*) has also been utilized to produce bactenecin as a pre-pro-peptide in *Bacillus*. The ability of these strains to inhibit the growth of SRB on SAE 1018 mild steel and 304 stainless steel in continuous reactors has been characterized.

Materials and Methods

Bacterial Strains, Plasmids and Growth Media.

*E. coli* XLI (Blue) {recA1 endA1gyrA96 thi-1 hsdR17 supE44 relA1 lac [F' proAB lacI$^q$ZDM15 Tn10 (Tet$^r$)]} was purchased from Stratagene (LaJolla, Calif.). *B. subtilis* BE1500 {trpC2, metB10, lys-3, Δ aprE66, Δ npr-82, Δ sacB::ermC} and plasmid pBE92 containing the alkaline protease (apr) promoter, signal sequence, and the alkaline phosphatase reporter gene were obtained from E. I. du Pont de Nemours Inc. (Wilmington, Del.). The protease-deficient strain *B. subtilis* WB600 (Wu, X.-C. et al., *J. Bacteriol.* 173(16):4952–4958 (1991)) (hereafter, Wu et al., 1991) {trpC2, Δ nprE, Δ aprA, Δ epr, Δ bpf, Δ mpr, Δ nprB} was obtained from Dr. Sui-Lam Wong (University of Calgary, Alberta, Canada). *B. polymyxa* was obtained from the American Type Culture Collection (ATCC 10401). *D. vulgaris* (ATCC strain 29579) was used as the reference SRB in this study. All corrosion experiments with *B. subtilis* BE1500 and *P. fragi* K (Jayaraman, A. et al., 1997a) were carried out in modified Baar's medium (ATCC medium 1249) for sulfate-reducing bacteria. Corrosion experiments with *B. polymyxa* were performed in modified Baar's medium supplemented with $\frac{1}{10}^{th}$ volume of 10× TY medium (10 g tryptone, 5 g yeast extract in 100 mL $H_2O$).

Enzymes and Chemicals.

All restriction enzymes, T4 DNA ligase, and Taq polymerase were obtained from Promega (Madison, Wis.). BCIP (5-bromo-4-chloro-3-indolyl phosphate) was purchased from Sigma Chemical Co. (St. Louis, Mo.). Indolicidin (free-acid form, 76% purity) and bactenecin (32% purity) were synthesized by Genosys Biotechnologies Inc. (The Woodlands, Tex.).

Plasmid Construction.

Recombinant DNA methods were performed as described by Maniatis (Maniatis, T. et al., 1982) and Rodriguez and Tait (Rodriguez, R. L. et al., *Recombinant DNA techniques, An introduction*, The Benjamin/Cummings Publishing Company Inc., Menlo Park, Calif. (1983)). Plasmid DNA was isolated from *Bacillus* according to the procedure of Bramucci and Nagarajan (Bramucci, M. G. and V. Nagarajan, *Appi. Environ. Microbiol*. 62(1 1):3948–3953 (1996)) (hereafter, Bramucci, 1996). The amino acid sequences for non-amidated indolicidin [Ile-Leu-Pro-Trp-Lys-Trp-Pro-Trp-Trp-Trp-Pro-Trp-Arg-Arg (SEQ ID NO:8)] (Selsted et al., 1992) and bactenecin [Arg-Leu-Cys-Arg-Ile-Val-Val-Ile-Arg-Val-Cys-Arg (SEQ ID NO:9)] (Romeo et al., 1988) were used to design oligonucleotides which encode the genes for these peptides. Plasmid pBE92-Ind was designed to express non-amidated indolicidin as a 12 amino acid peptide fused to the apr signal sequence, pBE92-Bac was designed to express bactenecin as a 13 amino acid peptide fused to the apr signal sequence, and pBE92-ProBac was designed to express bactenecin fused to the pro-region of the extracellular RNase barnase from *B. amyloliquefaciens* (Paddon, C. J. et al., *J. Bacteriol*. 171(2):1185–1187 (1989)) (hereafter, Paddon et al., 1989) and the apr signal sequence.

The synthetic oligos (FIG. 1) were synthesized by Gibco-BRL Life Technologies (Long Island, N.Y.) at a 200 nmole scale with polyacrylamide gel electrophoresis (PAGE) purification. The oligos were synthesized with flanking Hind III and Nhe I restriction sites with an additional six bases at either end for efficient restriction digestion. Two fully complementary oligos of each construct were resuspended in TE buffer (50 ng/μL), mixed at equimolar ratios, and incubated in boiling water for 3 minutes. The oligos annealed in the water bath as they cooled to room temperature (approximately two hours). The annealed oligos were digested with Hind III and Nhe I overnight, ethanol precipitated at −85° C. for one hour, and resuspended in deionized, distilled $H_2O$. Plasmid vector pBE92 was isolated from *E. coli* XLI (Blue) cell extracts using a plasmid midi kit (Qiagen Inc., Chatsworth, Calif.), and the DNA was digested with Hind III, Nhe I, and Sal I simultaneously for 14 hours at 37° C. The triple-digested vector and the antimicrobial gene insert were ligated at 16° C. for 17 hours at an insert:vector molar ratio of 28:1. The ligation mixture was extracted with phenol/chloroform/isoamyl alcohol (25:24:1), ethanol precipitated, and resuspended in 30 μL of dd$H_2O$.

Pro-bactenecin was synthesized as two oligo strands with a 21 base pair complementary region with Hind III and Nhe I restriction sites at the ends of the two strands (FIG. 2). A Not I site was also engineered downstream of the stop codon which served to introduce a unique site into pBE92. The two strands were annealed as described above, and the complementary regions were completed using Taq polymerase (one cycle, 30 secs at 94° C., followed by 30 secs at 55° C., and two hours at 72° C.) with a Perkin-Elmer thermal cycler N801–0150 (Perkin Elmer, Norwalk, Conn.). The final product was extracted with phenol/chloroform/isoamyl alcohol, ethanol precipitated at −85° C. in the presence of 1 mM $MgCl_2$ for one hour, and resuspended in 50 µL dd$H_2O$.

Transformants were identified by restriction digests with Bgl I (indolicidin), BssH II (bactenecin), and Not I (Probactenecin), and confirmed using a modification of the Boehringer-Mannhein colony-lift assay. Two hundred nanograms of plasmid DNA (from mini-preps of E. coli putative transformants with antimicrobial genes) was spotted on positively charged nylon membranes (Product No. 1209272, Boehringer Mannheim, Indianapolis, Ind.) and probed according to the manufacturer's specifications using antimicrobial gene synthetic oligo DNA (FIG. 1) labeled using the random primed DNA labeling protocol from Boehringer Mannheim.

Transformation of E. coli and Bacillus.

E. coli XLI (Blue) cells were made electrocompetent according to the method of Smith and Iglewski (Smith, A. W. et al., Nuc. Acids. Res. 17:10509 (1989)). Ten µL of the ligation mixture was used to electroporate the bacteria (1.2 kV/cm, 200 Ohms, 25 µF) using a gene pulser/pulse controller (Bio-Rad Laboratories, Hercules, Calif.), and clones containing the correct insert (pBE92-Indolicidin, pBE92-Bactenecin, and pBE92-ProBactenecin) were selected on LB agar plates containing 100 µg/mL of ampicillin and 40 µg/mL of BCIP using a blue/white selection technique (transformants with the correct insert produced white colonies while the reclosed vector resulted in blue colonies).

B. subtilis BE1500 was made competent and transformed according to the two-step method of Cutting and Vander Horn (Genetic analysis, p. 27–74, In C. R. Harwood and S. Cutting, M. (ed.), Molecular biological methods for Bacillus, John Wiley & Sons, New York (1990)). Late-exponential-phase competent cells were incubated with plasmid DNA (approximately 1 µg isolated from E. coli XLI (Blue)) for 30 minutes. The cultures were diluted with 1-mL of 10% yeast extract and incubated in a rotary shaker (New Brunswick Scientific, Edison, N.J., series 25 shaker) at 37° C. prior to plating on LB agar plates containing 25 µg/mL of kanamycin. B. polymyxa competent cells were prepared according to the procedure of Rosado et al. (J. Microbiol. Meth. 19:1–11 (1994)). Approximately 1 µg of DNA (pBE92-based constructs) isolated from B. subtilis BE1500 (Nagarajan, V. et al., Gene 114:121–126 (1992)) using the procedure of Bramucci and Nagarajan (Bramucci, 1996) was used to electroporate B. polymyxa (6.25 kV/cm, 200 Ohms, 25° F.). Cells were then incubated at 37° C. for 3 hours with shaking and selected on LB agar plates containing 150 µg/mL of kanamycin.

SDS-PAGE

B. subtilis BE1500 containing the plasmid pBE92-based constructs expressing the antimicrobial peptide genes was grown in 25 mL of LB medium to late-exponential phase (O.$D_{600}$=0.70–1.0) at 37° C. The cells were collected by centrifugation at 10,000×g for 10 mins at 4° C., and the supernatant was concentrated 25-fold using a SpeedVac concentrator (Model 200H, Savant Instruments Inc., Holbrook, N.Y.). The concentrated supernatant was mixed with a 2× sample buffer (0.125 M Tris-base, 0.4% SDS, 20% glycerol, and 0.1 mL of 1 mg/mL bromophenol blue with 5 µL 2-mercapto ethanol added for every 100 µL 2× buffer), boiled 5 min, and electrophoresed on a 16.5% Tris-Tricine gel (Bio-Rad, Hercules, Calif.).

Continuous Corrosion Experiments.

Batch culture corrosion experiments using SAE 1018 mild steel coupons (2.5 cm diameter, 1.2 mm thick) were performed in triplicates in 250 mL Erlenmeyer flasks at 30° C. without shaking as described previously (Jayaraman et al., 1997a). A continuous reactor (Jayaraman et al., 1997c) was also used to develop biofilms on 304 stainless steel and monitor corrosion using electrochemical impedance spectroscopy (EIS) in a minimum of two independent reactors using a Solarton-Schlumberger electrochemical measurement unit (SI 1280, Schlumberger Technical Instruments Division, San Jose, Calif.) interfaced to a Macintosh computer (PowerMac 7100/80, Apple Computers, Cupertino, Calif.) running EISIS electrochemical experimentation software (University of California, Irvine) (similar commercial software, THALES, can also be used). The open circuit potential (OCP) was measured as the potential between the metal specimen and a Ag/AgCl reference electrode, and the polarization resistance ($R_p$) was determined as the low-frequency value of the impedance (where the imaginary part of the impedance was zero or negligible). Continuous culture corrosion rates were estimated as the inverse of the polarization resistance (Macdonald, D. D. and M. C. H. McCubre, Applications of impedance spectroscopy, p. 262–267. In J. R. Macdonald (ed.), Impedance spectroscopy: Emphasizing solid materials and systems, John Wiley & Sons, New York (1987); Stern, M., Journal of Electrochemical Society, 105(11):638–647 (1958)).

Antimicrobial Assays.

To determine the susceptibility of the hosts B. subtilis BE1500 and B. polymyxa to the expressed antimicrobials, these strains were grown from a single colony in 25 mL of LB medium with shaking at 37° C. to an O.$D_{600}$ of 0.40–0.45. One mL aliquots were collected, washed with fresh LB medium and resuspended in 100 µL fresh LB medium in sterile eppendorf tubes. The antimicrobials indolicidin and bactenecin were added (50–100 µg/mL) and the tubes were incubated at 30° C. for one hour without shaking. Appropriate dilutions were spread on LB agar plates and incubated overnight at 37° C. to determine the extent of survival. The results were confirmed by performing two independent experiments.

Expression of indolicidin and bactenecin in Bacillus was determined in duplicates by exposing E. coli BK6 in suspension to concentrated culture supernatants. E. coli BK6 was grown to an O.$D_{600}$ of 0.20–0.25, pelleted at room temperature, and resuspended in different volumes (50 or 100 µL) of the concentrated supernatant. The cell suspension was incubated at 30° C. for 1 hour without aeration, and appropriate dilutions were plated on LB agar plates to determine the antimicrobial activity of the supernatant.

The ability of the supernatant from the B. subtilis constructs to inhibit SRB in suspension was determined by resuspending 500 µL of a late-exponential phase D. vulgaris culture (O.$D_{600}$=0.15–0.20) in an equal volume of 25-fold concentrated culture supernatant from B. subtilis BE1500 with the antimicrobial constructs under anaerobic conditions as described in the previous example. The cells were incubated at 30° C. for one hour and the surviving SRB enumerated using the three-tube most-probable-number (MPN) assay (Greenberg, 1992).

To determine the number of viable SRB in the biofilm by the three-tube MPN method, the biofilm was rinsed once in sterile water to remove loosely attached cells, scraped from 304 stainless steel coupons (2.5 cm diameter, 1.2 mm thick), resuspended, and serially diluted in fresh modified Baar's medium under anaerobic conditions as described by Jayaraman et al. The number of aerobic bacteria in the biofilm was determined by plating appropriate dilutions on LB agar plates.

RESULTS

Susceptibility of Expression Hosts to Antimicrobial Peptides.

B. subtilis BE1500 and B. subtilis WB600 showed several thousand times more susceptibility to the purified antimicrobial peptide indolicidin (non-amidated form, 50 and 100 μg/mL), and several-hundred-fold more susceptibility to the purified peptide bactenecin (50 μg/mL) after one-hour exposure at 30° C. than did B. polymyxa (see Table II). Therefore, B. polymyxa is a better host than the other species tested for expressing the antimicrobial peptides tested since it is resistant to both the non-amidated indolicidin and bactenecin.

TABLE II

Susceptibility of host strains to purified antimicrobials after one hour exposure at 30° C.

| | Fold-reduction in cell number | | |
|---|---|---|---|
| Bacterium | Indolicidin 50 μg/mL | Indolicidin 100 μg/mL | Bactenecin 50 μg/mL |
| B. subtilis BE1500 | 6000 | 10,000 | 100 |
| B. polymyxa 10401 | 4 | 4 | 2 |
| B. subtilis WB600 | 20,000 | 40,000 | 400 |

Cloning of Antimicrobial Peptides Using an E. coli Shuttle Vector.

Bacterial expression systems were constructed using the E. coli-Bacillus shuttle vector pBE92 to generate pBE92-Ind, pBE92-Bac, and pBE92-ProBac which utilize the apr promoter and signal sequence to express constitutively and secrete the antimicrobial peptides in Bacillus. The alkaline phosphatase gene in pBE92 was replaced by a Nhe I-Hind III insert containing the last three amino acids (Ser-Ala-Ser) of the apr signal sequence and the complete antimicrobial gene.

Detection of Antimicrobial Peptides Secreted by Bacillus.

Purified indolicidin (non-amidated form) was detectable by Coomassie staining when loaded at 230 ng/well but was not detected when loaded at 23 ng/well. Purified indolicidin and bactenecin were also not detectable using silver staining at a 250 ng/well loading. Western blots with rabbit-generated polyclonal antibodies to indolicidin (1:250 dilution) using B. subtilis BE1500 (pBE92-Ind) culture supernatants (concentrated 25-fold) did not reveal a band corresponding to indolicidin; however, the antibody was not specific to indolicidin and bound to many cellular proteins. The primary amino acid sequence of bactenecin indicated significant difficulty in generating polyclonal antibodies (Dr. Shing-Erh Yen, Zymed Laboratories Inc., personal communication); hence, polyclonal antibodies were not synthesized against this peptide.

Antimicrobial Activity of Indolicidin and Bactenecin in Bacillus Culture Supernatants Against E. coli and D. vulgaris in Suspension Cultures and in Biofilms.

The ability of concentrated culture supernatant from B. subtilis BE1500 with the antimicrobial plasmids to kill E. coli BK6 and D. vulgaris was determined. No reduction in the viability of E. coli BK6 and D. vulgaris was observed for the negative-control experiments in which supernatants from B. subtilis BE1500 (pBE92) and B. subtilis BE1500 (pBE92-Ind) were used (Table III); however, nearly 93% killing of E. coli BK6 and 83% killing of D. vulgaris was observed with supernatants from B. subtilis BE1500 (pBE92-Bac) and B. subtilis BE1500 (pBE92-ProBac). This result indicates that bactenecin was expressed, secreted into the culture supernatant, and that the disulfide bond was processed properly in the extracellular environment to form cyclic active bactenecin. (E. coli was used in these studies as a positive control to show that the peptide was expressed and active, as well as to show that the inhibition of the SRB was due to the peptide and not to exposure to oxygen or other exogenous causes.)

The number of viable SRB after five days in a biofilm on 304 stainless steel with B. subtilis BE1500 expressing the cloned antimicrobials was enumerated by the three-tube MPN assay (Table IV). Nearly 60-fold less SRB was present in the biofilm formed by B. subtilis BE1500 (pBE92-Bac) than biofilms formed by B. subtilis BE1500 (pBE92) and B. subtilis BE1500 (pBE92-Ind), while 10-fold less SRB was found with B. subtilis BE1500 (pBE92-Probac).

TABLE III

Susceptibility of E. coli BK6 and D. vulgaris to concentrated culture supernatants from B. subtilis BE1500 expressing antimicrobials. Data are the average of two independent experiments.

| | E. coli BK6 | | D. vulgaris | |
|---|---|---|---|---|
| | CFU/mL | Inhibition (%) | MPN/mL | Inhibition (%) |
| fresh medium | $9 \times 10^7$ | 0 | $8.29 \times 10^5$ | 0 |
| buffer + kanamycin 100 μg/mL | $4 \times 10^3$ | 99.996 | — | — |
| B. subtilis BE1500 (pBE92) | $8.7 \times 10^7$ | 3 | $8.29 \times 10^5$ | 0 |
| B. subtilis BE1500 (pBE92-Ind) | $7.9 \times 10^7$ | 12 | $8.29 \times 10^5$ | 0 |
| B. subtilis BE1500 (pBE92-Bac) | $6 \times 10^6$ | 93 | $1.43 \times 10^5$ | 87 |
| B. subtilis BE1500 (pBE92-ProBac) | $7 \times 10^6$ | 92 | $1.43 \times 10^5$ | 83 |

TABLE IV

Inhibition of SRB (determined by the MPN assay) in an aerobic biofilm of B. subtilis BE1500 biofilm expressing the antimicrobial plasmids on 304 stainless steel after five days. Data are from a biofilm from two independent experiments.

| Plasmid | Viable SRB MPN/mL | Inhibition | Viable B. subtilis BE1500, CFU/mL |
|---|---|---|---|
| pBE92 | $5.13 \times 10^5$ | 0 | $2.3 \times 10^8$ |
| pBE92-Indolicidin | $3.59 \times 10^5$ | 30 | $2.3 \times 10^8$ |
| pBE92-Bactenecin | $8.64 \times 10^3$ | 98 | $1.9 \times 10^8$ |
| pBE92-Probactenecin | $5.13 \times 10^4$ | 90 | $6.2 \times 10^8$ |

Batch and Continuous Culture Corrosion Studies with Bacillus Strains that Produce Cloned Antimicrobial Peptide.

The ability of the antimicrobial-producing constructs to inhibit the growth of SRB on SAE 1018 mild steel in quiescent shake flasks was studied. Upon addition of SRB ($O.D_{600}=0.16-0.20$) to a non-antimicrobial-producing P. fragi K culture, a strong odor of hydrogen sulfide was detected in less than 18 hours. This was also accompanied by the formation of an iron sulfide black precipitate which indicates growth and colonization of SRB in the aerobic biofilm grown on the metal surface. B. subtilis BE1500 was capable of delaying the onset of SRB corrosion by 36–48 hours compared to *P. fragi* K (as evidenced by the delay of appearance of an iron sulfide precipitate and the odor of hydrogen sulfide).

All the three antimicrobial-producing constructs in *B. subtilis* BE1500 were able to delay the onset of SRB corrosion by 96–120 hours compared to *P. fragi* K and *B. subtilis* BE1500. Replenishing the growth medium after seven days, however, resulted in the appearance of a black precipitate within 36 hours with all strains.

Addition of SRB to a 304 stainless steel continuous reactor with *P. fragi* K decreased the impedance value at the lowest frequency measured ($1.4 \times 10^{-3}$ Hz) by 5-fold within 36 hours of SRB addition. This decrease was also accompanied by the odor of hydrogen sulfide from the reactor outlet, and the reactor turned grey due to the formation of iron sulfide. The low-frequency phase angle also decreased (c.f., 82° vs. 68°). A similar change in the impedance spectra was also observed with the negative controls *B. subtilis* BE1500 (data not shown) and *B. subtilis* BE1500 (pBE92) (FIG. 3), although the change was delayed further by 24 hours. In contrast, the three antimicrobial-producing constructs were capable of decreasing the extent of change of the impedance spectra (FIG. 3). The indolicidin construct was least effective in inhibiting SRB and the low-frequency phase angle changed from 80° to 69°; however, it was still less than that observed with the control pBE92 (80° to 61°). The bactenecin constructs (with and without the pro-region) were more effective than the indolicidin construct and the low frequency phase angle decreased only to 76°. These results indicated that the growth of SRB on 304 stainless steel had been inhibited significantly by the bactenecin constructs.

Similar results were also obtained with *B. subtilis* WB600 (a strain deficient in six extracellular proteases) (Wu et al., 1991) expressing the cloned antimicrobials (FIG. 4). Addition of SRB to *B. subtilis* WB600 (pBE92) and *B. subtilis* WBN600 (pBE92-Ind) biofilms on 304 stainless steel decreased the low-frequency phase angle by 350 and 170 respectively; correspondingly, the low-frequency impedance also decreased by 7-fold and 5.5-fold respectively. However, no such decrease was observed with both bactenecin-expressing biofilms although the bactenecin construct appeared to be slightly more effective than the probactenecin construct (FIG. 4). This suggests that the processing of the pro-region to release mature bactenecin was inefficient in this protease-deficient strain.

Batch and Continuous Culture Corrosion Studies with a *Bacillus* Strain Producing a Cloned Antimicrobial in Addition to a Naturally Produced Antimicrobial.

The ability of *B. polymyxa* ATCC 10401 (which produces the peptide antimicrobial polymyxin) to inhibit the colonization of SRB on mild steel was studied in batch and continuous cultures. In batch cultures, *B. polymyxa* was able to delay the onset of SRB corrosion by 60 hours compared to a non-antimicrobial-producing *P. fragi* K. Replenishing the growth medium did not result in immediate colonization of the metal by SRB (as seen with both *P. fragi* K and *B. subtilis* BE1500) and no black precipitate was detected for 72 hours. Thus, the polymyxin-producing *B. polymyxa* was capable of delaying the growth of SRB in batch cultures.

In continuous reactors with 304 stainless steel, the addition of SRB did not alter the impedance spectra for nearly 250 hours (as opposed to 36 hours for the impedance spectra to change with *P. fragi* K, FIG. 5). No odor of sulfide was detected from the reactor outlet and the reactor did not increase in turbidity, as was observed with *P. fragi* K, *B. subtilis* BE1500, and *B. subtilis* WB600. Therefore, *B. polymyxa* was capable of inhibiting the growth of SRB on 304 stainless steel in continuous reactors.

Similar corrosion inhibition was also observed with the *B. polymyxa* having the antimicrobial constructs (FIG. 5) and the extent of inhibition was indistinguishable from that of the wild type strain.

DISCUSSION

The cationic antimicrobial peptides indolicidin and bactenecin were expressed constitutively in *B. subtilis* BE1500 as fusions to the signal peptide of the extracellular alkaline protease (apr) by an approach similar to Piers et al., 1993 and Pang et al. (1992). The synthetic oligos for indolicidin and bactenecin were designed as precise fusions to the signal sequence so that no additional amino acids were added to the N terminus of the peptide. This ensured that the expressed peptide would be maximally active and avoided the improper processing observed by Pang et al. (1992) whose expression system added 7 amino acids at the N terminus of the scorpion insectotoxin $I_5A$. Bactenecin was also produced as a pre-pro-peptide by inserting the DNA sequence for the pro-portion of the barnase from *B. amyloliquefaciens* (Paddon et al., 1989) between the signal peptide and the bactenecin gene. A similar fusion of pre-pro defensin resulted in complete prevention of proteolytic degradation of the secreted peptide in *S. aureus* (Piers et al., 1993) and has been attributed to the formation of a secondary structure between the anionic pro-region and the cationic peptide.

Indolicidin was expressed in *Bacillus* as the acid form, whereas in its naturally occuring form in bovine neutrophils, it is amidated at the C-terminus. The viability of *B. subtilis* was decreased by four-orders of magnitude by indolicidin, whereas *B. polymyxa* did not exhibit the same degree of sensitivity to indolicidin. This suggests that *B. subtilis* would not be an ideal expression host for expressing indolicidin in biofilms, especially as in a biofilm, indolicidin would not diffuse away as much as it would in a suspension culture and hence could attack the host cells.

The sensitivity of *E. coli* BK6 to concentrated culture supernatants from *B. subtilis* BE1500 was used as an indicator of antimicrobial activity of the supernatant as this bacterium is commonly used for evaluating the antimicrobial activity of cationic peptides (Romeo et al., 1988); Selsted et al., 1992). Our results indicate that the supernatant from *B. subtilis* BE1500 (pBE92-Ind) was not inhibitory to *E. coli* while the supernatant from *B. subtilis* BE1500 (pBE92-Bac) and *B. subtilis* BE1500 (pBE92-Probac) were active in reducing the viability of *E. coli* BK6.

In our continuous reactor experiments, we observed no difference in the growth of *B. subtilis* BE1500 (pBE92) and *B. subtilis* BE1500 (pBE92-Ind), which suggests poor expression of indolicidin. This was also corroborated by the lack of SRB-inhibition demonstrated with this construct in continuous reactors as inferred from changes in the impedance spectra (FIG. 3). *B. subtilis* BE1500 was more resistant to bactenecin than it was to indolicidin by a factor of 60 which could explain the ability of the bactenecin constructs to inhibit SRB on stainless steel.

Continuous reactor experiments with 304 stainless steel clearly demonstrated that the growth of SRB was inhibited (based both on qualitative indicators like the odor of hydrogen sulfide and iron sulfide precipitate and on the quantitative decrease in polarization resistance $R_p$). The bactenecin constructs were more effective than the indolicidin construct in inhibiting the growth of SRB, which suggests that bactenecin was expressed and processed properly to form a disulfide bond as defensins are usually inactive with improper disulfide bond processing (Piers et al., 1993). However, it was apparent that the SRB were not completely excluded from the biofilm as all reactors became more turbid upon the addition of SRB and a mild odor of sulfide was still detected from a reactor with *B. subtilis* BE1500 (pBE92-Bac). The inhibition of SRB with the bactenecin-producing construct compared to the control pBE92 was also corroborated by the 36-fold decrease in viable SRB present in a seven-day batch-culture biofilm on 304 stainless steel (Table IV). However, nearly $1 \times 10^4$ SRB/mL were detected even in the presence of bactenecin which confirms that SRB were not killed completely by the cloned antimicrobial peptides.

A polymyxin-producing *B. polymyxa* (wild type) was also able to delay the growth of SRB (and the onset of SRB-induced corrosion) in batch cultures on mild steel for 60 hours. Adding antimicrobial-producing plasmids to *B. polymyxa* did not significantly improve its ability to kill SRB on mild steel. But *B. polymyxa* grown on 304 stainless steel in continuous reactors was able to inhibit the growth of SRB completely (up to 275 hours). Our observations that *D. vulgaris* is unable to grow as a monoculture on stainless steel (whereas it can do so on mild steel) could also explain the effectiveness of these antimicrobials in inhibiting SRB on stainless steel only.

The data set forth in this example demonstrate that the growth of SRB on 304 stainless steel can be controlled by generating peptide antimicrobials from within the biofilm and illustrate its potential for use in preventing microbiologically influenced corrosion of steel. The effectiveness of *B. polymyxa* in inhibiting the growth of SRB provides the basis for optimizing a dual-killing system for combating SRB-induced corrosion where low levels of two antimicrobials (the naturally produced one and the cloned antimicrobial) could act simultaneously to inhibit SRB.

Example 5

Inhibition of SRB Colonization and Corrosion on Mild and Stainless Steel by Bacteria Secreting Antimicrobial Agents This example demonstrates inhibition of SRB colonization and anaerobic corrosion in biofilms on mild steel and stainless steel through the use of bacteria secreting antimicrobial agents.

The commonly used antibiotic ampicillin was used as a reference antimicrobial in this study to show that addition of an antimicrobial agent prior to SRB colonization can be a viable approach to reduce SRB-induced corrosion. As shown in the previous example, the 10 amino acid cyclic peptide gramicidin S inhibits SRB and was also added externally as a model peptide antibiotic to demonstrate the feasibility of producing peptide antimicrobials in biofilms to inhibit corrosion of mild steel and stainless steel. Furthermore, a gramicidin-S-overproducing *Bacillus brevis* 18 strain (Azuma et al., 1992) was used to establish a biofilm which secretes gramicidin S and inhibits SRB on stainless steel.

Materials and Methods
Bacterial Strains, Medium, and Growth Conditions.
All aerobic bacteria were grown from a single colony in 10 mL of modified Baar's medium (ATCC medium 1249) at 30° C. and 250 rpm (series 25 shaker, New Brunswick Scientific, Edison, N.J.) and used as the inoculum for biofilm development. *D. vulgaris* was cultivated in 15 mL screwcap tubes containing 10 mL of modified Baar's medium supplemented with 100 µL each of the oxygen-scavengers 4% sodium sulfide and Oxyrase (Oxyrase Inc., Mansfeld, Ohio). Initial cultures were grown from −85° C. glycerol stocks; all subsequent cultures were grown with a 3% inoculum from the initial culture at 30° C. without shaking. *D. vulgaris* was routinely cultured in tightly closed screwcap tubes and exposed to oxygen in air without any difficulty in cultivation as has been reported by Angell and White (1995, supra). *D. vulgaris* cultures were also cultured periodically in the presence of 0.1% ferrous ammonium sulfate, and the presence of sulfate-reducers was confirmed by the detection of black iron sulfide in the culture tubes. The desulfoviridin assay (Postgate, 1984) was also routinely performed with the detection of a pink color under UV light confirming the presence of *D. vulgaris*. Gramicidin S was obtained from Sigma Chemical Company (St. Louis, Mo.), chloramphenicol from Fisher Scientific (Pittsburgh, Pa.), and ammonium molybdate from Aldrich Chemical Company (St. Louis, Mo.).

Metal Coupon Preparation.

Mild steel SAE 1018 coupons for batch culture experiments (25.5 mm diameter and 1.2 mm thick) and SAE 1018 mild steel and stainless steel 304 plates for continuous culture experiments (7.5×7.5 cm squares, 1.2 mm thick) were cut from sheet stock and prepared as reported previously (Jayaraman, et al., 1997a).

Batch Culture Corrosion Experiments.

Batch culture corrosion experiments were performed in 250 mL Erlenmeyer flasks at 30° C. without shaking as described previously (Jayaraman, et al., 1997a). Mild steel coupons (triplicates) exposed to *D. vulgaris* were cleaned by wiping the surface with 0.01% chromic acid followed by repeated washes in warm water; all other coupons were cleaned as described earlier (Jayaraman, et al., 1997a). The specific mass loss (in mg/cm$^2$ for the total surface area of the coupon, 11.18 cm$^2$) was used as an indicator of the extent of corrosion, which was assumed to be uniform. The growth medium was replenished every 7 days and replaced (with appropriate antibiotics) by gentle addition along the walls of the flask. A 3% (vol/vol) SRB inoculum was added to the flasks after 3 days of aerobic biofilm development.

Continuous Culture Corrosion Experiments using EIS.

A continuous reactor was used to develop biofilms on metal surfaces as previously described (Jayaraman et al., 1997c). Electrochemical impedance spectroscopy (EIS) was used to obtain impedance data in at least duplicate experiments using a Solarton-Schlumberger electrochemical measurement unit (SI 1280, Schlumberger Technical Instruments Division, San Jose, Calif.) interfaced to a Macintosh computer (PowerMac 7100/80, Apple Computers, Cupertino, Calif.) running EISIS electrochemical experimentation software (University of California, Irvine) (THALES, a similar commercial software, can also be used). The open-circuit potential (OCP) was measured as the potential between the metal specimen and the reference electrode (Ag/AgCl), and the polarization resistance was determined as the dc limit of the impedance using the ANALEIS software developed by Mansfeld et al. (*ASTM Special Technical Protocol* 1154:186 (1992)). Continuous culture corrosion rates were estimated from the experimental polarization resistance $R_p$ based on the Stern-Geary equation $R_p = B/i_{corr}$, where B is a parameter depending on the Tafel slopes and $i_{corr}$ is the corrosion current density which can be converted into a corrosion rate using Faraday's law (Mansfeld, F., The polarization resistance technique for measuring corrosion currents, In Fontana, M. G., Staehle, R. W. (ed.), *Advances in Corrosion Science and Technology*, Plenum Press, New York (1976)).

A 3% (vol/vol) SRB inoculum (culture age 24–48 hours) was added to the reactor after 3 to 5 days of aerobic biofilm development. Based on the minimum inhibitory concentrations available in the literature (Saleh et al., 1964) and also on data generated in this laboratory on the susceptibility of SRB in suspension cultures to various inorganics and antimicrobials, ampicillin (200 µg/mL), chloramphenicol (200 µg/mL), both ampicillin (200 µg/mL) and chloramphenicol (100 µg/mL), and both ampicillin (200 µg/mL) and ammonium molybdate (200 µg/mL) were added to reactors (before or after SRB had colonized the metal) in an attempt to inhibit SRB. All antimicrobials were simultaneously added to the nutrient feed and the reactor at appropriate concentrations.

Enumeration of Viable SRB in Biofilms.

Aerobic biofilms were developed on 304 stainless steel coupons (25.5 mm diameter, 1.2 mm thick) in 250 mL Erlenmeyer flasks for two days with modified Baar's medium at 30° C. A 1.0% (vol/vol) inoculum of *D. vulgaris* ($O.D_{600}$=0.16–0.18) was added and allowed to colonize the biofilm for an additional four days. The metal coupons were carefully removed from the flasks and rinsed twice by immersing in distilled water to remove loosely attached cells. The biofilm was then scraped off with a sterile spatula and resuspended in 500 µL of modified Baar's medium. Aerobic bacteria were determined by plate counts and viable SRB were enumerated by the three-tube MPN assay (Greenberg, 1992, supra).

RESULTS

Batch and Continuous Corrosion with Non-antimicrobial-producing *P. fragi* K and *D. vulgaris* on SAE 1018 Mild Steel.

Mass loss from mild steel SAE 1018 coupons in modified Baar's medium in the presence of *P. fragi* K and *D. vulgaris* was examined for 28 days in stationary batch cultures at 30° C. Whenever *D. vulgaris* was present in the biofilm, the coupons were covered with a thick, black deposit and were difficult to clean. A dual-culture of *P. fragi* K and *D. vulgaris* produced a 1.8-fold increase in corrosion rate after 21 days of exposure compared to a monoculture of *P. fragi* K; however, the corrosion rate observed in both cases was always lower than that observed with sterile modified Baar's medium (Table V). The corrosion rate observed with a monoculture of *D. vulgaris* on SAE 1018 steel was higher than that in sterile medium after 14 days (1.4-fold) and 21 days (2.5-fold, extrapolated from Table V). When ampicillin (100 µg/mL) was added to the flasks before *D. vulgaris* was allowed to colonize the metal coupon, the mass loss observed was 40% (1 week) to 14% (3 weeks) less than that seen when ampicillin was added after SRB (Table V). Macroscopic examination of the metal coupons exposed to *D. vulgaris* revealed the presence of numerous pits for all these experiments.

The anaerobic *D. vulgaris* grew in continuous reactors as a monoculture with an airflow rate of 200 mL/min to the headspace as indicated by the development of a black iron sulfide precipitate and odor of hydrogen sulfide from the reactor outlet. Growth of *D. vulgaris* in continuous reactors increased $R_p$ by 90-fold after 72 hours compared to sterile controls. Addition of 200 µg/mL of ampicillin after 240 hours of SRB growth did not change $R_p$, and the reactor remained black with the distinct odor of sulfide from the exhaust (Table VI). A combination of 200 µg/mL of ampicillin and 200 µg/mL of ammonium molybdate after 320 hours cleared the reactor supernatant; however, the odor of sulfide was still detected indicating that the corrosion rate did not decrease and the growth of SRB was not inhibited.

The addition of *D. vulgaris* to a continuous *P. fragi* K reactor increased $R_p$ of mild steel by 3-fold after 36 hours and changed the frequency dependence of the phase angle; the reactor turned black and the odor of sulfide was detected from the reactor outlet (Table VI and FIG. 6). Prior to the addition of *D. vulgaris*, the impedance attained a steady asymptotic value at low frequency ($4.52 \times 10^4$ Ohms·cm$^2$); however, within 24 hours of SRB addition the reactor turned black, the odor of sulfide was detected, and the impedance no longer reached an asymptotic value at the lowest frequency ($1.4 \times 10^{-3}$ Hz). Addition of 200 µg/mL ampicillin (Table VI) and a combination of 100 µg/mL of ampicillin and 25 µg/mL of chloramphenicol after 120 and 150 hours of SRB growth (data not shown) also did not shift $R_p$ to its value prior to SRB addition, indicating that there was no inhibition of SRB.

TABLE V

Corrosion loss of SAE 1018 steel in batch cultures with dual-cultures of aerobic bacteria and a representative SRB.*

| Bacterial strain(s) | Antimicrobial produced | Corrosion loss, mg/cm$^2$ | | | | | | |
|---|---|---|---|---|---|---|---|---|
| | | 3 days | 7 days | 10 days | 14 days | 21 days | 28 days | 32 days |
| sterile medium | — | — | 0.54 ± 0.08 | 0.77 ± 0.11 | — | 1.03 ± 0.04 | — | 2.05 ± 0.11 |
| *P. fragi* K | None | 0.04 ± 0.01 | — | 0.19 ± 0.05 | 0.33 ± 0.05 | 0.38 ± 0.01 | | 0.43 |
| *P. fragi* K + SRB | None | 0.04 ± 0.01 | | 0.35 ± 0.01 | 0.52 ± 0.08 | 0.71 ± 0.08 | — | 0.86 ± 0.17 |
| *P. fragi* K + SRB + Amp 100 | None | 0.04 ± 0.01 | — | 0.35 ± 0.01 | 0.42 ± 0.04 | 0.56 ± 0.08 | — | 0.65 ± 0.07 |
| *P. fragi* K + Amp 100 + SRB | None | 0.04 ± 0.01 | — | 0.25 ± 0.04 | 0.33 ± 0.04 | 0.49 ± 0.07 | | — |
| *D. vulgaris* ATCC 29579 | None | 0.095 | 0.191 | | 1.225 | | 3.83 | — |
| *B. subtilis* ATCC 6633 | Subtilin | 0.13 ± 0.01 | 0.45 ± 0.08 | — | 0.57 ± 0.08 | — | — | — |
| *B. subtilis* ATCC 6633 + SRB | Subtilin | 0.13 ± 0.01 | 0.52 ± 0.03 | — | 0.81 ± 0.04 | — | — | — |
| *B. brevis* ATCC 35690 | Edeines | 0.07 ± 0.01 | 0.16 ± 0.03 | — | 0.19 ± 0.01 | — | — | — |
| *B. brevis* ATCC 35690 + SRB | Edeines | 0.07 ± 0.01 | 0.23 ± 0.04 | — | 0.28 ± 0.03 | — | — | — |
| *B. brevis* 18 | Gramicidin S | 0.09 ± 0.01 | 0.16 ± 0.02 | — | 0.28 ± 0.06 | — | 0.40 ± 0.06 | — |
| *B. brevis* 18 + SRB | Gramicidin S | — | 0.19 ± 0.02 | — | 0.30 ± 0.07 | — | 0.44 ± 0.06 | — |

*The order in which items are listed in the first column indicates the order in which they were added to the culture. For example, "*P. fragi* K + SRB + Amp 100" indicates that *P. fragi* K bacteria were added to the culture and allowed to establish themselves as a biofilm, SRB were added and allowed to establish themselves in the biofilm, and ampicillin was then added to the culture medium.

TABLE VI

Corrosion behavior of SAE 1018 steel in continuous reactors with dual cultures of aerobe and SRB after various methods to kill SRB.*

| Experiment | Antimicrobial added to kill SRB, μg/mL | Time elapsed after antimicrobial addition, hr | Reactor characteristics | $R^P$ (Ohm · cm$^2$) before SRB addition (days) | $R^P$ (Ohm · cm$^2$) after antimicrobial addition (days) | $R^P$ (Ohm · cm$^2$) from mass loss data in Table V (days) | EIS spectra |
|---|---|---|---|---|---|---|---|
| D. vulgaris (1 of 2 experiments) | Ampicillin (200 μg) added after 240 hours of SRB growth | 200 | Reactor turned black and outlet had odor of sulfide. No changes observed after antimicrobial addition | $3.58 \times 10^3$ (0) | $3.24 \times 10^5$ (10) | $5.7 \times 10^3$ (14) | not shown |
| P. fragi K + SRB + Ampicillin (1 of 2 experiments) | Ampicillin (200 μg) added after 120 hours of SRB growth | 200 | Reactor turned black and outlet had odor of sulfide. No changes after antimicrobial addition | $4.52 \times 10^4$ (2) | $1.35 \times 10^5$ (7) | $3.76 \times 10^4$ (14) | FIG. 6 |
| P. fragi K + Ampicillin + SRB (1 of 3 experiments) | Ampicillin (100 μg) added before SRB addition | 100 | Reactor did not turn black and outlet did not smell of sulfide | $4.52 \times 10^4$ (2) | $2.60 \times 10^4$ (9) | $2.00 \times 10^4$ (10) | FIG. 6 |
| P. fragi k + Gramicidin S + SRB (1 of 1 experiment) | Gramicidin S (100 μg) added before SRB addition | 80 | Reactor did not turn black, but outlet had odor of sulfide | $4.52 \times 10^4$ (2) | $3.89 \times 10^4$ (6) | Note 1 | FIG. 9 |
| B. brevis 18 + SRB (1 of 2 experiments) | Gramicidin S (produced in situ before SRB addition) | 48 | Reactor did not turn black, but outlet had odor of sulfide | $3.43 \times 10^4$ (3) | $5.78 \times 10^4$ (8) | $2.34 \times 10^4$ (14) | FIG. 9 |
| B. brevis 35690 (1 of 2 experiments) | Edeines (produced in situ before SRB addition) | 250 | Reactor did not turn black, but outlet had odor of sulfide | $3.75 \times 10^4$ (3) | not calculated | not calculated | not shown |

*The order in which items are listed in the first column indicates the order in which they were added to the culture. For example, "P. fragi K + SRB + Amp 100" indicates that P. fragi K bacteria were added to the culture and allowed to establish themselves as a biofilm, SRB were added and allowed to establish themselves in the biofilm, and ampicillin was then added to the culture medium.
Note 1. Not possible to calculate $R_P$ from impedance spectra based on available equivalent circuit models Continuous Corrosion Rates with Non-antimicrobial-producing P. fragi K and D. vulgaris on S.S. 304 Stainless Steel.

No difference was observed between the impedance spectra for sterile Baar's medium and with P. fragi K on 304 stainless steel after nearly 900 hours of exposure. D. vulgaris did not grow as a monoculture on 304 stainless steel, and the addition of D. vulgaris to a P. fragi K reactor changed the frequency dependence of the impedance at lower frequencies within 48 hours (FIG. 7). The phase angle showed a minimum value upon addition of SRB indicating the appearance of a new time constant at very low frequencies (FIG. 7), and the maximum value of the phase angle decreased from 81° to 69°.

The changes of the impedance spectra were accompanied by the detection of the odor of sulfide from the reactor outlet, and the reactor also turned gray. Addition of 200 μg/mL ampicillin (FIG. 7), both 200 μg/mL ampicillin and 100 μg/mL chloramphenicol (Table VII, second column), or both 200 μg/mL ampicillin and 200 μg/mL ammonium molybdate (data not shown) to a dual-culture reactor did not change the impedance spectra to the simple one-time-constant behavior observed prior to D. vulgaris addition (FIG. 7) or stop the production of hydrogen sulfide and iron sulfide, indicating that SRB had not been killed.

TABLE VII

Corrosion behavior of 304 stainless steel in continuous reactors with dual cultures of aerobe and after various methods to kill SRB*

| Experiment | Antimicrobials added to kill SRB, μg/mL | Time elapsed after antimicrobial addition, hr | Reactor characteristics | EIS spectra |
|---|---|---|---|---|
| P. fragi K + SRB + Ampicillin (1 of 3 experiments) | Ampicillin (200 μg) after 170 hrs and chloramphenicol (100 μg) added after 400 hours of SRB growth | 490 | Reactor turned grey and outlet had odor of sulfide upon SRB addition. No changes observed after antimicrobial addition | FIG. 7 |
| P. fragi K + Ampicillin + SRB (1 of 3 experiments) | Ampicillin (100 μg) added before SRB addition | 120 | Reactor never turned grey and outlet did not have odor of sulfide upon SRB addition. | FIG. 7 |
| P. fragi K + Gramicidin + SRB (1 of 1 experiment) | Gramicidin S (100 μg) added before SRB addition | 130 | Reactor never turned grey and outlet did not have odor of sulfide upon SRB addition. | FIG. 8 |

TABLE VII-continued

Corrosion behavior of 304 stainless steel in continuous reactors with dual cultures of aerobe and after various methods to kill SRB*

| Experiment | Antimicrobials added to kill SRB, μg/mL | Time elapsed after antimicrobial addition, hr | Reactor characteristics | EIS spectra |
|---|---|---|---|---|
| B. brevis + D. vulgaris (1 of 3 experiments) | Gramicidin S (produced in situ before SRB addition) | 150 | Reactor never turned grey and outlet had mild odor of sulfide upon SRB addition. | FIG. 8 |
| B. brevis 18 + (Nagano) + D. vulgaris (1 of 2 experiments) | Gramicidin S (produced in situ before SRB addition) | 190 | Reactor turned grey and outlet had odor of sulfide upon SRB addition. | not shown |

*The order in which items are listed in the first column indicates the order in which they were added to the culture. For example, "P. fragi K + SRB + Amp" indicates that P. fragi K bacteria were added to the culture and allowed to establish themselves as a biofilm, SRB were added and allowed to establish themselves in the biofilm, and ampicillin was then added to the culture medium.

Continuous Corrosion Rates with the Biofilm Exposed to Purified SRB-Inhibiting Antimicrobials Before Addition of D. vulgaris.

To determine if antimicrobials are effective in inhibiting SRB when added prior to SRB colonization, non-antimicrobial producing P. fragi K biofilms on SAE 1018 mild steel and 304 stainless steel were exposed to 100 μg/mL of ampicillin or gramicidin S for 24 hours before D. vulgaris was added. P. fragi K grew to saturation in overnight suspension cultures exposed to 100 μg/mL of both antimicrobials; therefore, it was not affected by adding these antimicrobials.

When D. vulgaris was added to mild steel and stainless steel reactors after the addition of ampicillin, no change in the impedance spectra and $R_p$ was observed up to 100 hours (FIGS. 6 & 7, Tables VI & VII). No odor of sulfide was detected in the reactor outlet; hence, D. vulgaris was completely inhibited in the reactors by this antimicrobial. External addition of the cyclic decapeptide antimicrobial gramicidin S at 100 μg/mL was also completely effective in inhibiting the growth of D. vulgaris in the 304 stainless steel experiments as evidenced by the capacitive nature of the impedance spectra (FIG. 7 and Table VI); however, with mild steel, the reactor turned grey although there was no increase in $R_p$ after 80 hours of exposure to SRB (FIG. 8 and Table VII). Hence, the onset of D. vulgaris-induced corrosion of mild steel was delayed as compared to P. fragi K and D. vulgaris without any gramicidin S present.

Batch and Continuous Corrosion Rates with Antimicrobial-producing Bacilli and D. vulgaris on SAE 1018 Mild Steel and 304 Stainless Steel.

Batch corrosion studies of SAE 1018 steel coupons with D. vulgaris and antimicrobial-producing Bacillus biofilms (based on their reported production of antimicrobial peptides, Table V) demonstrated that all the Bacilli were able to restrict the colonization of D. vulgaris for up to 1 week (evidenced by the smaller, 1.2 to 1.4-fold increases in corrosion rate, as compared to a larger, 1.8-fold increase for P. fragi K in modified Baar's medium, Table V, as well as on lack of development of black color and sulfide odor). When the medium was replenished after 7 days, however, all the flasks except those with B. brevis 18 turned black, and iron sulfide was detected within 24 hours. The increase in corrosion rate with D. vulgaris in the presence of the Bacilli (1.2 to 1.5-fold increase) was comparable to that seen with P. fragi K and D. vulgaris (1.6-fold increase). The mass loss observed with B. brevis 18 and SRB was comparable to that with P. fragi alone and nearly two-fold better than with P. fragi K and SRB (Table V). No odor of sulfide was detected throughout the experiment. The effectiveness of gramicidin S in inhibiting the growth of SRB in batch cultures was also corroborated by the three-orders-of-magnitude decrease in viable SRB detected (by the three-tube MPN assay) in a B. brevis 18 biofilm on 304 stainless steel after four days of growth compared to a non-antimicrobial-producing P. fragi K biofilm (c.f., $5.47 \times 10^2$/mL vs. $8.47 \times 10^5$/mL).

Continuous culture corrosion rates with B. brevis 18, a gramicidin S hyper-producing strain (Azuma, et al., 1992) were obtained in the presence of D. vulgaris on SAE 1018 mild steel (FIG. 9 & Table VI); the increase in $R_p$ as observed upon addition of D. vulgaris to P. fragi K on mild steel was delayed by 24 hours. Eventually, SRB seem to have colonized the biofilm as evidenced by the odor of hydrogen sulfide from the reactor outlet; however, $R_p$ remained constant at $5.78 \times 10^4$ ohms·cm² as opposed to $3.43 \times 10^4$ ohms·cm² before SRB addition.

FIG. 8 and Table VII show that the addition of D. vulgaris to a B. brevis 18 biofilm on type 304 stainless steel did not decrease $R_p$ after 120 hours, even though the smell of sulfide was detected in the reactor outlet 48 hours after the addition of D. vulgaris. Therefore, the gramicidin S producing B. brevis 18 was capable of inhibiting the colonization of SRB on 304 stainless steel, while it could only delay the growth of SRB on SAE 1018 mild steel.

DISCUSSION

D. vulgaris was chosen as the representative sulfate-reducing bacterium to study the effectiveness of in-situ-produced antimicrobials in inhibiting anaerobic corrosion as it has been reported to accelerate corrosion (Gaylarde, 1992), and strains of this species have the ability to withstand oxygen stress (Hardy, J. A., Hamilton, W. A., Curr. Microbiol. 6:259–262 (1981)). D. vulgaris showed remarkable resilience in growing as a monoculture in stationary batch cultures and continuous reactors with an oxygen-saturated headspace and in corroding mild steel coupons as was evidenced by the black discoloration of the medium (Gaylarde, 1992, supra). D. vulgaris was also able to grow within an aerobic biofilm in shake flasks under conditions of oxygen saturation in the headspace above the liquid as well as in continuous reactors with an air flow rate of 200 mL/min into the reactor headspace. The growth conditions for D. vulgaris in this study were very similar to those used by Gaylarde (1992, supra) as well as Hamilton and Lee (1995) (Biocorrosion, p. 243–264, In Barton, L. L. (ed.), Sulfate-reducing Bacteria, Plenum Press, New York) and have been termed as most aggressive when a small amount of oxygen is present in a SRB culture which leads to maximum corrosion rates.

Mild steel coupons exposed to batch cultures with *P. fragi* K and *D. vulgaris* showed an increase in corrosion rates compared to exposure to monocultures of *P. fragi* K which was similar to that reported by Jack et al. (*Corr. Sci.* 33:1843–1853 (1992)) and Gaylarde (1992, supra). Addition of various combinations of antibiotics to batch cultures to inhibit growth of *D. vulgaris* did not prove successful in inhibiting corrosion (Table V). However, batch cultures of antimicrobial-producing *Bacilli* were capable of delaying the onset of SRB-induced corrosion compared to a monoculture control up to 7 days. This SRB-inhibitory effect decreased considerably with most *Bacillus* after the growth medium was replenished. Since most antimicrobials are secondary metabolites (Bailey, J. E., Ollis, D. F., *Biochemical Engineering Fundamentals* Second ed. McGraw-Hill Publishing Company, New York (1986)) and are produced during the stationary phase of growth (Doi, R. H., McGlouglin, M. 1992. *Biology of Bacilli*. Application to industry. Butterworth-Heinemann, Boston, Mass. (1992)), replenishing the growth medium after 7 days could have removed the majority of the antimicrobial present in the biofilm and allowed *D. vulgaris* to colonize the metal surface before inhibitory levels of antimicrobial were produced again. *B. brevis* 18, however, completely inhibited the growth of SRB up to 28 days due to the overproduction of gramicidin S as a result of mutagenesis used to make this strain (Azuma, et al., 1992). This result indicated the potential of gramicidin S in killing SRB and demonstrated not only that antimicrobials could be successfully introduced prior to SRB colonization via other bacteria in the biofilm, but also that antimicrobial compounds introduced in this manner successfully inhibited the growth of SRB.

Impedance spectra of mild steel and stainless steel were used to characterize the corrosion behavior observed in continuous cultures with these metals. Addition of *D. vulgaris* to *P. fragi* K on SAE 1018 in the mild steel reactors increased $R_p$ which indicates the corrosion rate was decreased. This seemingly contradictory observation could be explained due to the formation of an oxide layer at the metal surface; since modified Baar's medium has a pH of 7.5 (neutral), the rust layer formed does not dissolve as would be expected in a more acidic environment. This buildup of rust could cause an increase in $R_p$ and an apparent decrease in the corrosion rate. The validity of the conclusions from EIS regarding the inhibition of SRB can be verified by the good correlation between $R_p$ values calculated from the batch culture mass loss experiments and those obtained with EIS for mild steel (Table VII).

A simple one-time-constant (OTC) was observed with *P. fragi* K and *P. fragi* K+ampicillin+SRB (FIG. 6) on mild steel which is typical for uniform corrosion in neutral media (Mansfeld, F., Lorenz, W. J., Electrochemical impedance spectroscopy (EIS): Application in corrosion science and technology, In Varma, R., Selman, J. R. (ed.), *Techniques for characterization of electrodes and electrochemical processes*, John Wiley & Sons, New York (1991)) (hereafter Mansfeld and Lorenz, 1991), and the $R_p$ and capacitance values (C) obtained for these two experiments were similar (Table VII). For *P. fragi* K+SRB on mild steel, the frequency dependence of the phase angle φ at the lowest frequencies suggests the occurrence of a new time constant which could be due to pitting while the symmetrical frequency dependence of φ for *P. fragi* K+SRB+ampicillin and the shift of the entire impedance curve compared to that for *P. fragi* K could be due to a higher $R_p$ (FIG. 6). Similar capacitance values were indicated in the spectra for *P. fragi* K+SRB and *P. fragi* K+SRB+ampicillin on mild steel; however, it was not possible to fit these spectra to a simple equivalent circuit and obtain quantitative values of $R_p$ and C. The impedance spectra for *B. brevis* 18, *B. brevis* 18+SRB, and *P. fragi* K+gramicidin S+SRB on mild steel exhibited the frequency dependence usually observed for uniform corrosion, and $R_p$ could be determined as the dc limit (φ=0°) of the impedance modulus |Z| (FIG. 9).

Stainless steel samples exposed to reactors with sterile medium also did not reach a steady low-frequency impedance value. The lack of difference in the impedance spectra between sterile controls and reactors on 304 stainless steel with *P. fragi* K or *B. brevis* indicates that very little corrosion occurred during the period. This result is similar to the observations of Hernandez et al., 1994, who did not observe a steady low-frequency impedance value with mild steel in nine salts solution for 20 days and attributed it to the lack of corrosion.

The 304 stainless steel spectra for *P. fragi* K and *P. fragi* K+ampicillin+SRB were capacitive with high $R_p$ values close to $2 \times 10^7$ Ohm·cm$^2$ and capacitance values between 100 and 200 μF/cm$^2$; this indicates uniform corrosion typical of stainless steel in neutral media (Mansfeld and Lorenz, 1991). A deviation from purely capacitive behavior similar to that for mild steel was observed with *P. fragi* K+SRB and *P. fragi* K+SRB+ampicillin on 304 stainless steel (FIG. 7), and it was not possible to fit these impedance data to a simple EC. A new time constant was observed for *P. fragi* K+SRB as indicated by the minimum of φ at about 0.01 Hz (FIG. 7). The impedance spectra for *B. brevis* 18, *B. brevis* 18+SRB, and *P. fragi* K+gramicidin S+SRB were all capacitive, and the $R_p$ and C values observed with *B. brevis* 18 and *B. brevis* 18+SRB were similar to those observed with *P. fragi* K (FIG. 8).

While the extent of changes in corrosion rates for all exposure conditions cannot be accurately determined without fitting the experimental data to appropriate equivalent circuits, one can conclude that corrosion rates increased due to the production of hydrogen sulfide upon SRB addition. Similarly the changes in the phase angle of 304 stainless steel upon addition of SRB (FIG. 7b) indicate the occurrence of additional electrochemical processes and suggest localized corrosion (Mansfeld and Lorenz, 1991). Hence, the absence of changes in the impedance spectra when purified antimicrobials were present prior to the addition of SRB or when gramicidin S was generated by the biofilm demonstrates the inhibition of SRB on stainless steel (FIG. 8).

Ampicillin and chloramphenicol are known to inhibit suspension cultures of *D. vulgaris* at 1 μg/mL and 3 μg/mL, respectively (Odom and Singleton, 1993). Since biofilms are known to be 10 to 1000 times more resistant to biocides (Cheung and Beech, 1996), up to 200 μg/mL of both antibiotics were used in this study. However, when added after SRB had colonized the metal surface, these additives did not stop further production of sulfide or decrease the corrosion rates of either type of steel. This is consistent with the observations of Franklin et al. (1991) (*Corrosion* 47:128–134) who observed that SRB may be able to survive exposure to halogen biocides for at least 26 hours and that of Franklin et al. (1989) (An analogue MIC system with specific bacterial consortia, to test effectiveness of materials selection and countermeasures, Presented at the Corrosion 89, New Orleans, La., National Association of Corrosion Engineers, Houston, Tex.), who reported a 3- to 4-orders-of-magnitude decrease in a biofilm population with biocide addition, but noted that the population reached its pretreatment density within 24 hours of stopping the biocide dose. A similar observation was made with mild steel reactors in this study; when ampicillin containing medium was discontinued, the onset of SRB-induced corrosion was evident within 36 hours.

Example 6

Use of the Method to Inoculate a Water Cooling Tower Against SRB-Related Corrosion This example demonstrates the use of the invention to "inoculate" a water cooling tower against SRB-related corrosion. A new water cooling tower is installed in a power plant. When the tower is ready to enter service, a culture of *Bacillus polymyxa* recombinantly altered to secrete bactenicin at a concentration of about 1–10 μg/mL, is added to a water supply at a concentration of about $10^3$ to about $10^6$ cells/mL, preferably in a dilute, inexpensive complex nutrient broth such as Luria Bertani, which is then circulated through the water tower. Before the water used to "inoculate" the tower dries, the normal service water supply to the tower is connected and normal operation of the tower commences.

Example 7

Use of the Method to Protect an Existing Structure

This example demonstrates use of the method to treat a pipeline already in service. A scraping is made of the surface a wet portion of the pipeline and the bacteria in the biofilm of the pipeline are cultured. One or more of the cultured Gram-positive bacterial species (preferred because such bacteria have only a single cell membrane through which to secrete antimicrobial or anticorrosive agents, or both) are selected based on criteria such as the ease and reliability of genetic transformation and of culturing. The Gram-positive bacteria selected are then transformed by conjugation with a chromosomal insertion vector, such as pCNB5, encoding the gene for bactenecin. The transformed bacteria are cultured and then tested to confirm secretion of the anti-SRB agent. Cultures testing positive for secretion of the anti-SRB agent are then grown up in quantity and aliquots of the resulting culture are introduced into the pipeline at intervals, at resulting concentrations of $10^3$ to about $10^6$ cells/ml.

All publications, and patent applications cited in this specification are herein incorporated by reference in their entirety as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed is:

1. A system for inhibiting corrosion of a material selected from the group of a corrosion sensitive material and a degradation sensitive material, comprising a material having a biofilm on its surface, said biofilm comprising an aerobic bacterium not normally present in the biofilm, which bacterium secretes a chemical composition in an amount sufficient to inhibit the growth of sulfate reducing bacteria on the material.

2. The system of claim 1, wherein the corrosion sensitive material is a metal.

3. The system of claim 2, wherein the metal is steel.

4. The system of claim 3, wherein the steel is mild steel.

5. The system of claim 3, wherein the steel is stainless steel.

6. The system of claim 2, wherein the metal is aluminum or an aluminum alloy.

7. The system of claim 2, wherein the metal is copper or a copper alloy.

8. The system of claim 2, wherein the metal is selected from the group consisting of titanium, nickel, a titanium alloy and a nickel alloy.

9. The system of claim 1, wherein the degradation sensitive material is concrete.

10. The system of claim 1, wherein the degradation sensitive material is reinforced concrete.

11. The system of claim 1, wherein the degradation sensitive material is cement.

12. The system of claim 1, wherein the bacterium is of the genus *Bacillus*.

13. The system of claim 1, wherein the bacterium is of the genus *Pseudomonas*.

14. The system of claim 1 wherein the chemical composition is an antibiotic.

15. The system of claim 14, wherein the antibiotic is selected from the group gramicidin S, indolicidin, polymyxin, and bactenecin.

16. The system of claim 1, wherein the bacterium further secretes a chemical composition selected from the group consisting of polyaspartate, polyglutamate, polyglycine, and a siderophore.

17. A system for of inhibiting the growth of sulfate-reducing bacteria on a material selected from the group of a corrosion-sensitive material and a degradation-sensitive material, comprising a material having a biofilm on its surface, said biofilm comprising a bacterium recombinantly altered to secrete a chemical composition in amounts higher than do wild-type members of its species, which amounts secreted by the bacterium are sufficient to inhibit the growth of sulfate-reducing bacteria on the material.

18. The system of claim 17, wherein the corrosion sensitive material is a metal.

19. The system of claim 18, wherein the metal is steel.

20. The system of claim 19, wherein the steel is selected from the group consisting of mild steel and stainless steel.

21. The system of claim 18, wherein the metal is selected from the group consisting of aluminum, an aluminum alloy, copper, and a copper alloy.

22. The system of claim 17, wherein the degradation sensitive material is concrete.

23. The system of claim 17, wherein the degradation sensitive material is reinforced concrete.

24. The system of claim 17, wherein the degradation sensitive material is cement.

25. The system of claim 17, wherein the bacterium is an aerobe.

26. The system of claim 17, wherein the bacterium is selected from the genus *Pseudomonas* and the genus *Bacillus*.

27. The system of claim 17, wherein the chemical composition is an antibiotic.

28. The system of claim 17, wherein the chemical composition is selected from the group consisting of polyaspartate, polyglutamate, polyglycine, and a siderophore.

29. A system for inhibiting corrosion of a material selected from the group of a corrosion sensitive material and a degradation sensitive material, comprising a material having a biofilm on its surface, said biofilm comprising a bacterium, which bacterium is recombinantly altered to secrete a chemical composition which inhibits the growth of sulfate-reducing bacteria, which chemical composition is not secreted by wild-type members of the species.

30. The system of claim 29, wherein the corrosion sensitive material is a metal.

31. The system of claim 29, wherein the metal is steel.

32. The system of claim 31, wherein the steel is selected from the group consisting of mild steel and stainless steel.

33. The system of claim 29, wherein the metal is selected from the group consisting of aluminum, an aluminum alloy, copper, and a copper alloy.

34. The system of claim 29, wherein the degradation sensitive material is concrete.

35. The system of claim 29, wherein the degradation sensitive material is reinforced concrete.

36. The system of claim 29, wherein the degradation sensitive material is cement.

37. The system of claim 29, wherein the bacterium is an aerobe.

38. The system of claim 29, wherein the bacterium is selected from the genus *Pseudomonas* and the genus *Bacillus*.

39. The system of claim 29, wherein the chemical composition is an antibiotic.

40. The system of claim 39, wherein the antibiotic is selected from the group gramicidin S, indolicidin, polymyxin, and bactenecin.

41. The system of claim 29, wherein the bacteria further secrete a chemical composition selected from the group consisting of polyaspartate, polyglutamate, polyglycine, and a siderophore.

42. A system of claim 1, wherein said material is (a) above-ground, (b) exposed to the environment, or (c) immersed in water in contact with air.

43. A system of claim 1, wherein said material is part of a water cooling system, heating or cooling system, storage vessel, heat exchanger, fire protection system, fuel system, sewage system, storm drainage system, municipal drainage system, bridge support, railway support, or highway support.

44. A system for inhibiting bacterial or fungal corrosion of a fuel tank or fuel system, said system comprising a fuel tank or fuel system having at least one surface on which is a bacterium not normally present on said surface, which bacterium secretes a chemical composition in an amount sufficient to inhibit the growth of corrosion-causing bacteria or fungus on the fuel tank or fuel system.

45. A system of claim 44, wherein said bacterium secreting said chemical composition is of the genus *Serratia*.

46. A system of claim 44, wherein said chemical composition is one not normally secreted by said bacterium or which is secreted in amounts larger than are normally secreted by said bacterium.

* * * * *